(12) United States Patent
Mayeux et al.

(10) Patent No.: US 9,044,491 B2
(45) Date of Patent: *Jun. 2, 2015

(54) METHOD FOR IMPROVING BLOOD FLOW USING STILBENOID DERIVATIVES

(75) Inventors: Philip R. Mayeux, Little Rock, AR (US); Joseph H. Holthoff, Little Rock, AR (US)

(73) Assignee: The Board of Trustees of the University of Arkansas, Little Rock, AK (US)

( * ) Notice: Subject to any disclaimer, the term of this patent is extended or adjusted under 35 U.S.C. 154(b) by 350 days.

This patent is subject to a terminal disclaimer.

(21) Appl. No.: 13/339,150

(22) Filed: Dec. 28, 2011

(65) Prior Publication Data

US 2012/0165280 A1 Jun. 28, 2012

Related U.S. Application Data

(60) Provisional application No. 61/521,128, filed on Aug. 8, 2011, provisional application No. 61/427,614, filed on Dec. 28, 2010.

(51) Int. Cl.
*A61K 31/7034* (2006.01)
*A61P 9/10* (2006.01)
*A61P 13/12* (2006.01)

(52) U.S. Cl.
CPC ............................... *A61K 31/7034* (2013.01)

(58) Field of Classification Search
USPC ........ 514/35, 521, 532, 617, 679; 560/37, 57; 564/171
See application file for complete search history.

(56) References Cited

U.S. PATENT DOCUMENTS

| | | | |
|---|---|---|---|
| 6,448,450 B1 * | 9/2002 | Nag et al. ..................... | 568/646 |
| 6,552,085 B2 * | 4/2003 | Inman et al. .................. | 514/576 |
| 7,384,920 B2 * | 6/2008 | Li et al. ........................ | 514/23 |
| 2012/0184536 A1 | 7/2012 | Radominska-Pandya | |

FOREIGN PATENT DOCUMENTS

| | | | |
|---|---|---|---|
| WO | 99/59561 A2 | 11/1999 | |
| WO | WO 99/59561 | * 11/1999 | ............ A61K 31/00 |

OTHER PUBLICATIONS

Langenberg et al, Critical Care 2008, 12R38, pp. 1-7.*
Liu et al , Biochemical Journal, 2000, 346, part. 2, pp. 835-840.*
Kolgazi et al, Journal of Surgical Research, 2006, 134, 315-321.*
Non-Final Office Action from related U.S. Appl. No. 13/339,163, dated Jul. 12, 2013, 15 pgs.
Merck Manual, 1992, 16th Edition, pp. 446-447; 522-523, 1274.
Liu et al., "Functional CB1 cannabinoid receptors in human vascular endothelial cells," Biochemical Journal, 2000, pp. 835-840, vol. 346.
Olas et al., "Comparative studies of the antioxidant effects of a naturally occurring resveratrol analogue—trans-3,3',5,5'-tetrahydroxy-4'-methoxystilbene and resveratrol—against oxidation and nitration of biomolecules in blood platelets," Cell Biology and Toxicology, 2008, pp. 331-340, vol. 24.
Office Action from related U.S. Appl. No. 13/339,163, dated Jan. 29, 2014; 19 pgs.
Office Action from related U.S. Appl. No. 13/339,163, dated Aug. 6, 2014; 17 pgs.
Office Action from related U.S. Appl. No. 13/339,163, dated Dec. 24, 2014; 25 pgs.
Warn et al., "Infrared body temperature measurement of mice as an early predictor of death in experimental fungal infections", Lab. Animals, 2003, pp. 126-131, vol. 37.
Wu et al., "Evidence for the Role of Reactive Nitrogen Species in Polymicrobial Sepsis-Induced Renal Peritubular Capillary Dysfunction and Tubular Injury", J. Am. Soc. Nephroi., 2007, pp. 1807-1815, vol. 18.

* cited by examiner

*Primary Examiner* — Ganapathy Krishnan
(74) *Attorney, Agent, or Firm* — Polsinelli PC

(57) ABSTRACT

The present invention generally provides methods for using stilbenoid derivatives to improve blood flow and microcirculation.

20 Claims, 28 Drawing Sheets

(3 of 28 Drawing Sheet(s) Filed in Color)

METHOD FOR IMPROVING BLOOD FLOW USING STILBENOID DERIVATIVES

CROSS REFERENCE TO RELATED APPLICATIONS

This application claims the priority of U.S. provisional application No. 61/521,128, filed Aug. 8, 2011, and U.S. provisional application No. 61/427,614, filed Dec. 28, 2010, each of which is hereby incorporated by reference in its entirety.

GOVERNMENTAL RIGHTS

This invention was made with government support under DK085705 and DK075991 awarded by the National Institutes of Health. The government has certain rights in the invention.

FIELD OF THE INVENTION

The present invention generally relates to stilbenoid derivatives. In particular, it relates to the use of stilbenoid derivatives to increase blood flow and microcirculation.

BACKGROUND OF THE INVENTION

There is an increasing demand for effective natural, non-toxic therapeutic agents to treat or prevent diseases, improve human health and promote longevity. Trans-resveratrol (tRes), a naturally occurring plant stilbenoid has been the focus of great attention because it is an efficacious antioxidant and anti-inflammatory agent with numerous potential therapeutic applications. Few natural compounds with such a broad spectrum of activities resulting from simultaneous interactions with multiple molecular targets and showing such impressive health benefits have been identified. For example, tRes and its analogs have been shown to be effective scavengers of reactive nitrogen species. RNS play a role in several diseases including sepsis (inflammatory response elicited by microbial infection). Sepsis affects approximately 18 million people worldwide on an annual basis. Current therapies to treat sepsis include efforts to increase the macrocirculation of patients, however, restoration of macrocirculation is not always sufficient to restore microcirculation and preserve organ function.

Although initial pre-clinical studies are encouraging, the oral bioavailability of native, free tRes following rapid absorption is poor due to swift conjugation to glucuronides and sulfates. Additionally, tRes is a strong inhibitor of several important enzymes of the cytochrome P450 (CYP) system. The rapid metabolism of tRes generally is viewed as the critical barrier to clinical development of this potentially valuable therapeutic agent. Increasing the dose of tRes, however, may not be a good option to overcoming its limited bioavailability because this could lead to unpredictable drug interactions via alterations in CYP metabolism.

Because of the enormous therapeutic potential of tRes, there is a need for improved tRes analogs with increased bioavailability and longer half-lives. Such analogs or derivatives may have enhanced biological properties and, consequently, improved therapeutic efficacy. Similarly, there is a need for the identification of the molecular targets of tRes and its analogs because such information may lead to the design and development of improved therapeutic agents.

SUMMARY OF THE INVENTION

Briefly, therefore, the present invention provides a method for improving blood flow and microcirculation in a subject. The method comprises administering a monomer or an oligomer of a compound comprising Formula (I) or a derivative thereof to the subject, wherein the blood flow and microcirculation of the subject are improved. The compound comprising Formula (I) has the following structure:

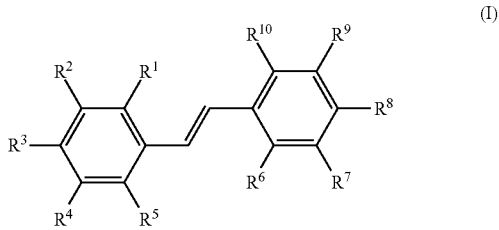

wherein:
$R^1$, $R^2$, $R^3$, $R^4$, $R^5$, $R^6$, $R^7$, $R^8$, $R^9$, and $R^{10}$ are independently chosen from hydrogen, hydroxyl, hydrocarbyl, substituted hydrocarbyl, hydrocarbyloxy, substituted hydrocarbyloxy, and sulfoxy; provided that at least one of the R groups is a hydroxyl or substituted hydroxyl group; and provided that if the compound comprising Formula (I) is monomeric, then the compound comprising Formula (I) is other than resveratrol.

In another aspect, the present invention provides a method for improving renal blood flow and microcirculation during sepsis. The method comprises administering a monomer or an oligomer of a compound comprising Formula (I) or a derivative thereof to a subject experiencing sepsis, such that the blood flow and microcirculation of the subject are improved. The compound comprising Formula (I) has the following structure:

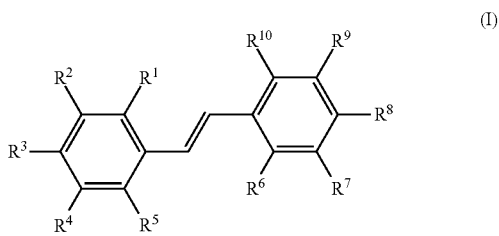

wherein:
$R^1$, $R^2$, $R^3$, $R^4$, $R^5$, $R^6$, $R^7$, $R^8$, $R^9$, and $R^{10}$ are independently chosen from hydrogen, hydroxyl, hydrocarbyl, substituted hydrocarbyl, hydrocarbyloxy, substituted hydrocarbyloxy, and sulfoxy; provided that at least one of the R groups is a hydroxyl or substituted hydroxyl group; and provided that if the compound comprising Formula (I) is monomeric, then the compound comprising Formula (I) is other than resveratrol.

Yet another aspect of the invention provides a method for preventing progression of acute kidney injury during sepsis. The method comprises administering a monomer or an oligomer of a compound comprising Formula (I) or a derivative thereof to a subject experiencing sepsis, such that progression of acute kidney injury in the subject is prevented. The compound comprising Formula (I) has the following structure:

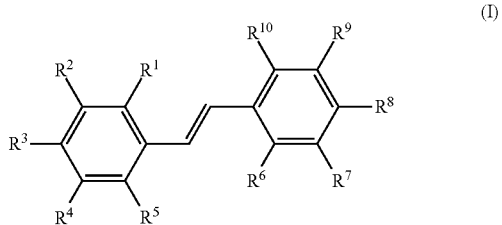

wherein:
$R^1$, $R^2$, $R^3$, $R^4$, $R^5$, $R^6$, $R^7$, $R^8$, $R^9$, and $R^{10}$ are independently chosen from hydrogen, hydroxyl, hydrocarbyl, substituted hydrocarbyl, hydrocarbyloxy, substituted hydrocarbyloxy, and sulfoxy; provided that at least one of the R groups is a hydroxyl or substituted hydroxyl group; and provided that if the compound comprising Formula (I) is monomeric, then the compound comprising Formula (I) is other than resveratrol.

Other features and iterations of the invention are described in more detail below.

REFERENCE TO COLOR FIGURES

This application file contains at least one photograph executed in color. Copies of this patent application publication with color photographs will be provided by the Office upon request and payment of the necessary fee.

DETAILED DESCRIPTION OF THE INVENTION

Figure 1:
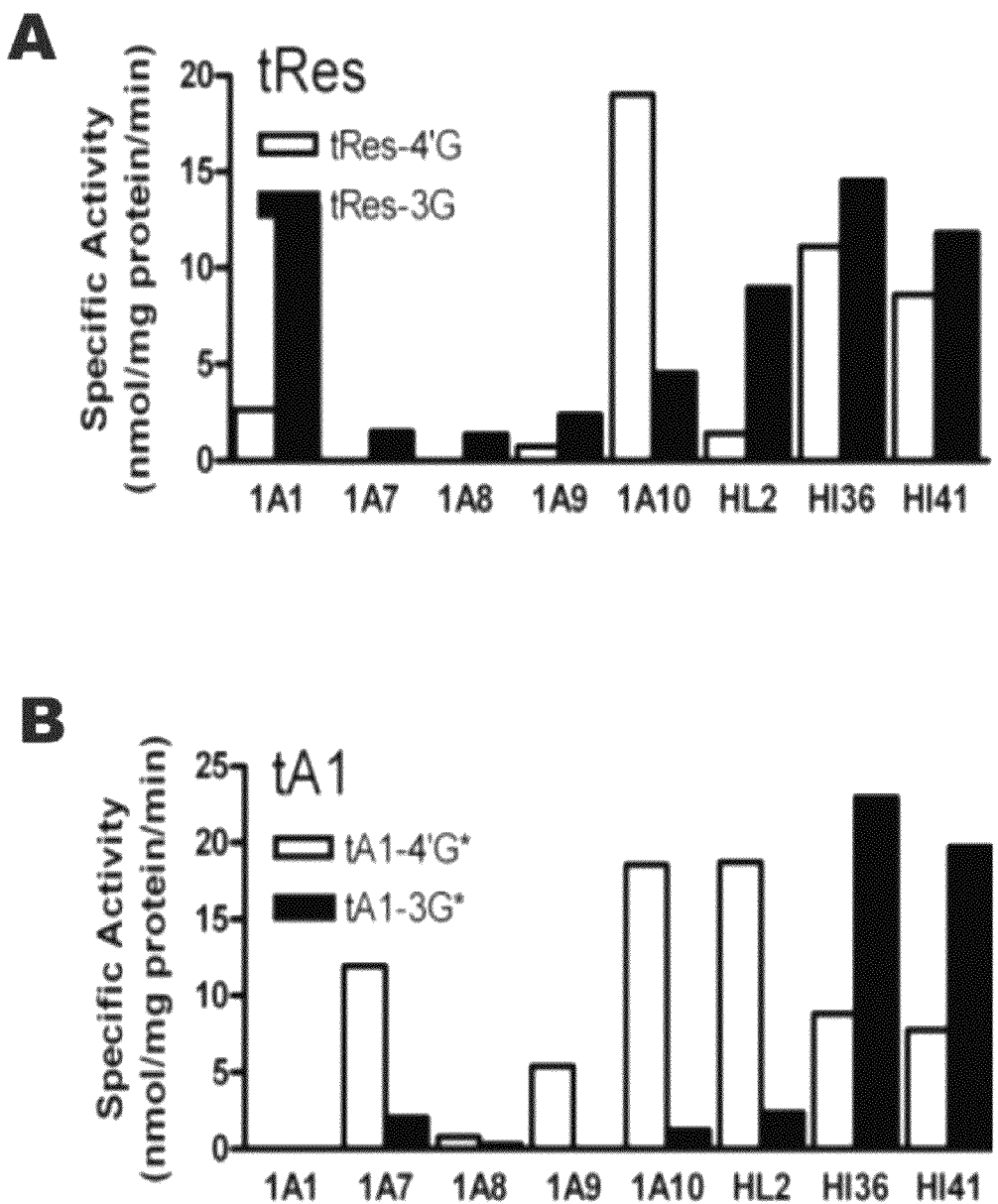
FIG. 1 illustrates the ability of human UGT isoforms (1A1, 1A7, 1A8, 1A9, 1A10), human liver microsomes (HL2), and human intestinal microsomes (HI36, HI41) to glucuronidate (A) trans-resveratrol (tRes), (B) trans-arachidin-1 (tA1), (C) trans-piceatannol (tPice), and (D) trans-arachidin-3 (tA3). Plotted is the specific activity of each isoform or enzyme preparation for 4'-glucuronidates (open bars) and 3'-glucuronidates (solid bars). * Postulated assignments based on HPLC elution order.
Figure 1:
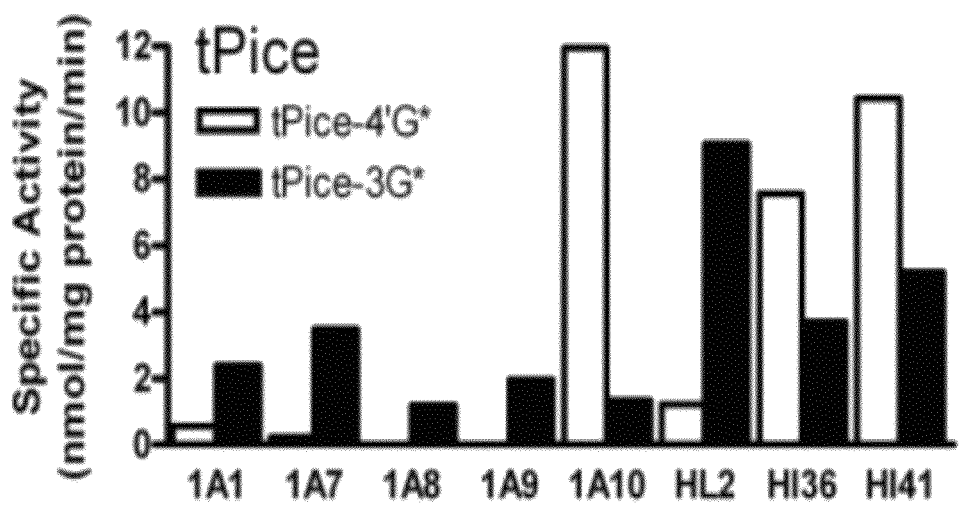
Figure 1:
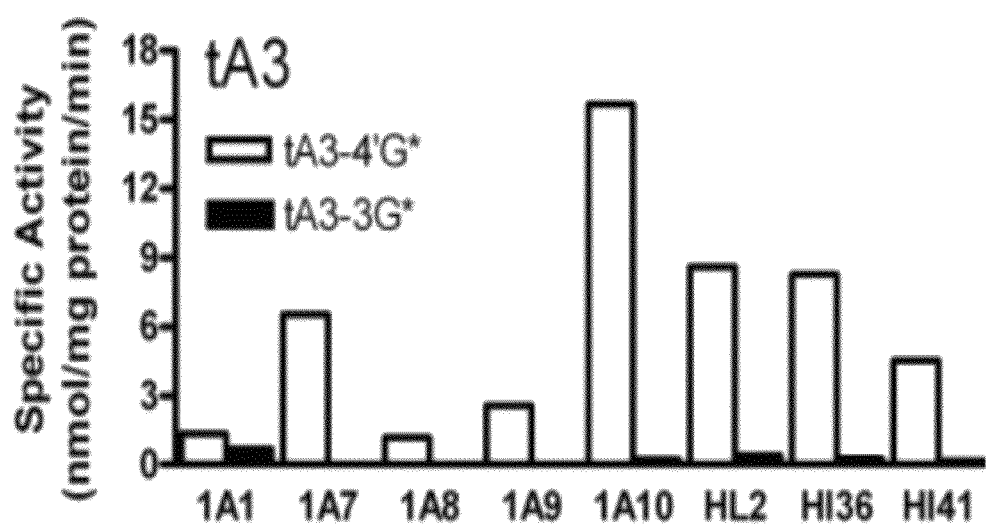
Figure 2A:
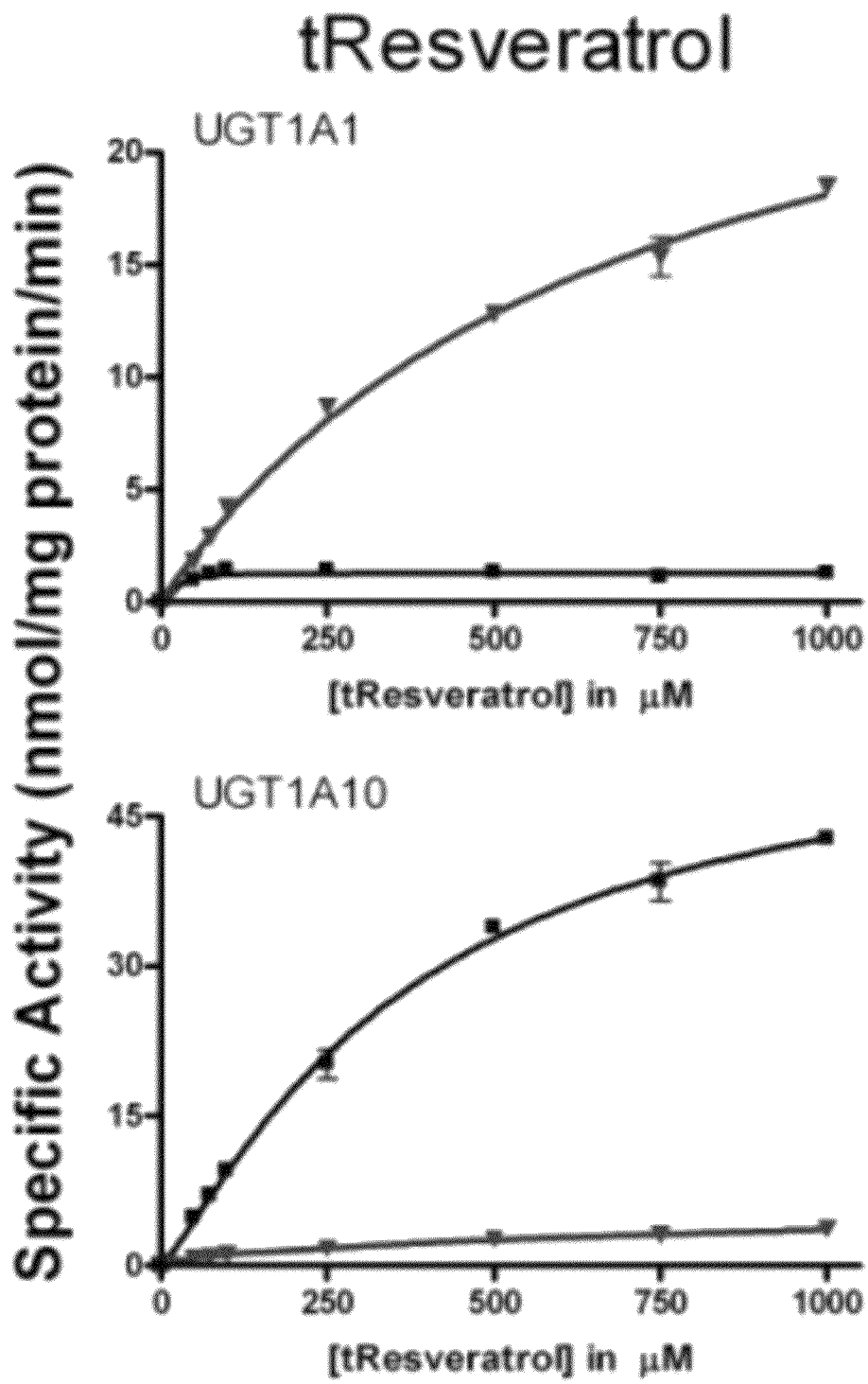
FIG. 2 depicts the kinetic analysis of glucuronidation. (A) trans-resveratrol, (B) trans-piceatannol, (C) trans-arachidin-1, and (D) trans-arachidin-3. Plotted is the specific activity of human UGT1A1 (upper plots) and UGT1A10 (lower plots) as a function of substrate concentration.
Figure 2B:
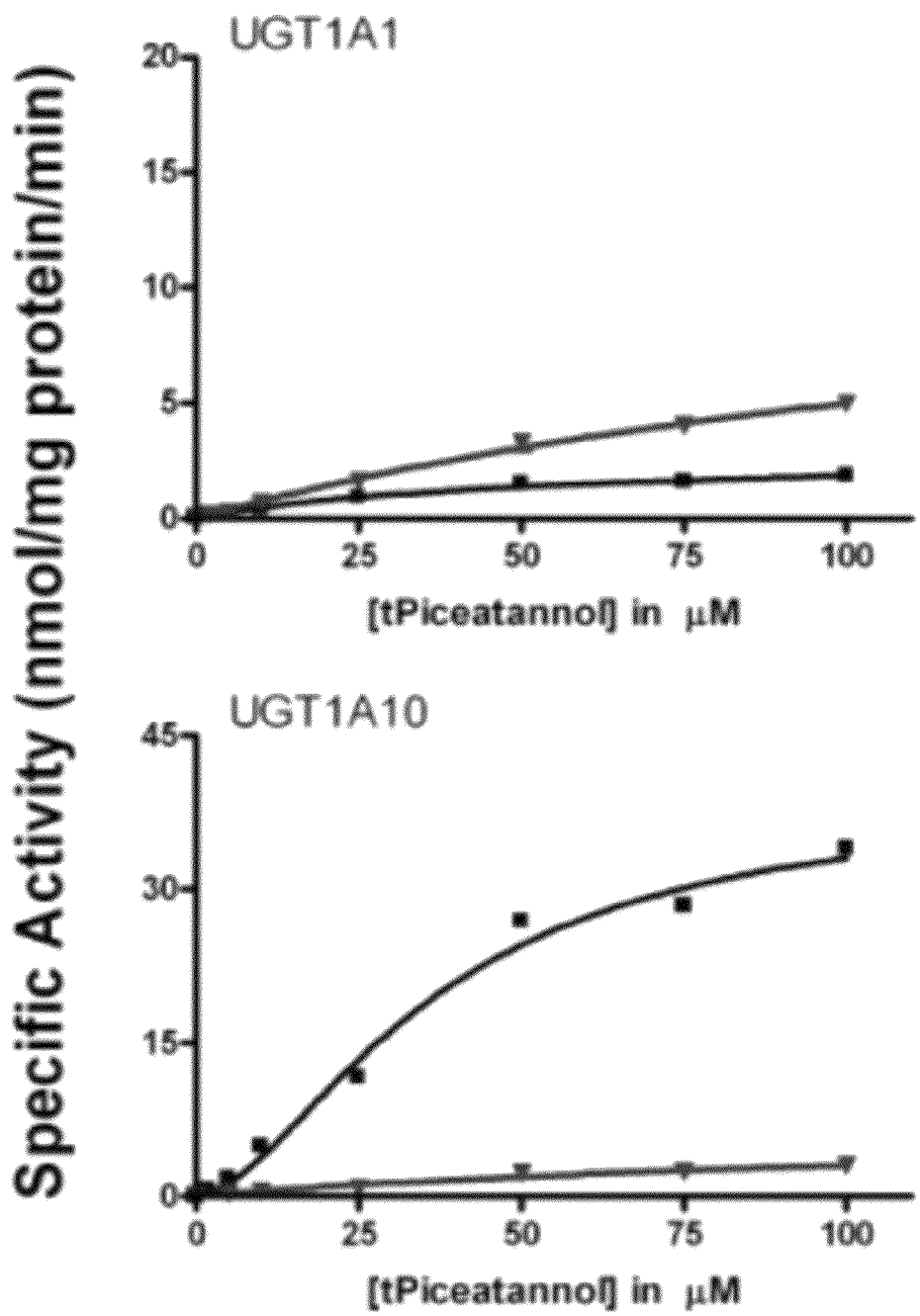
Figure 2C:
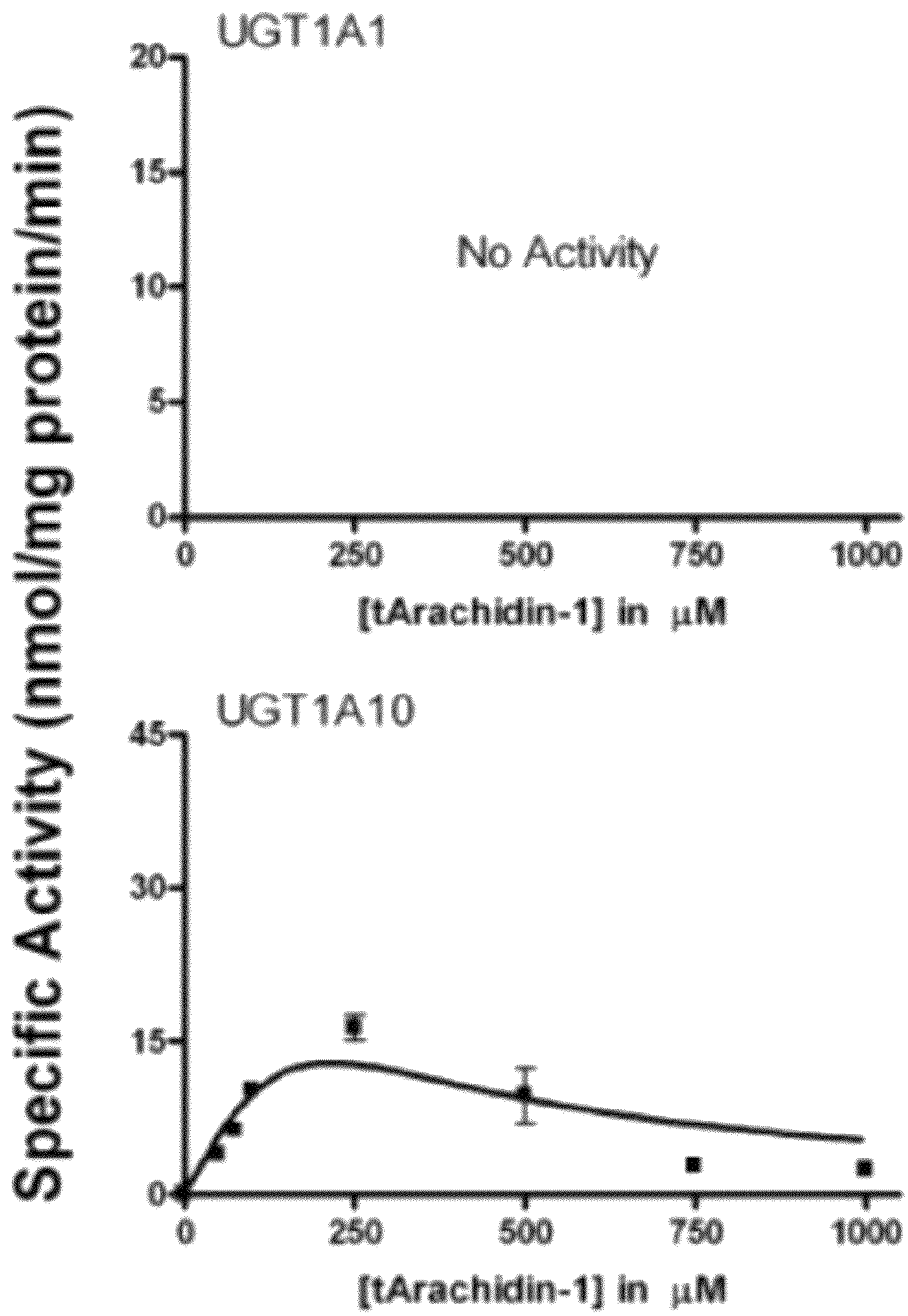
Figure 2D:
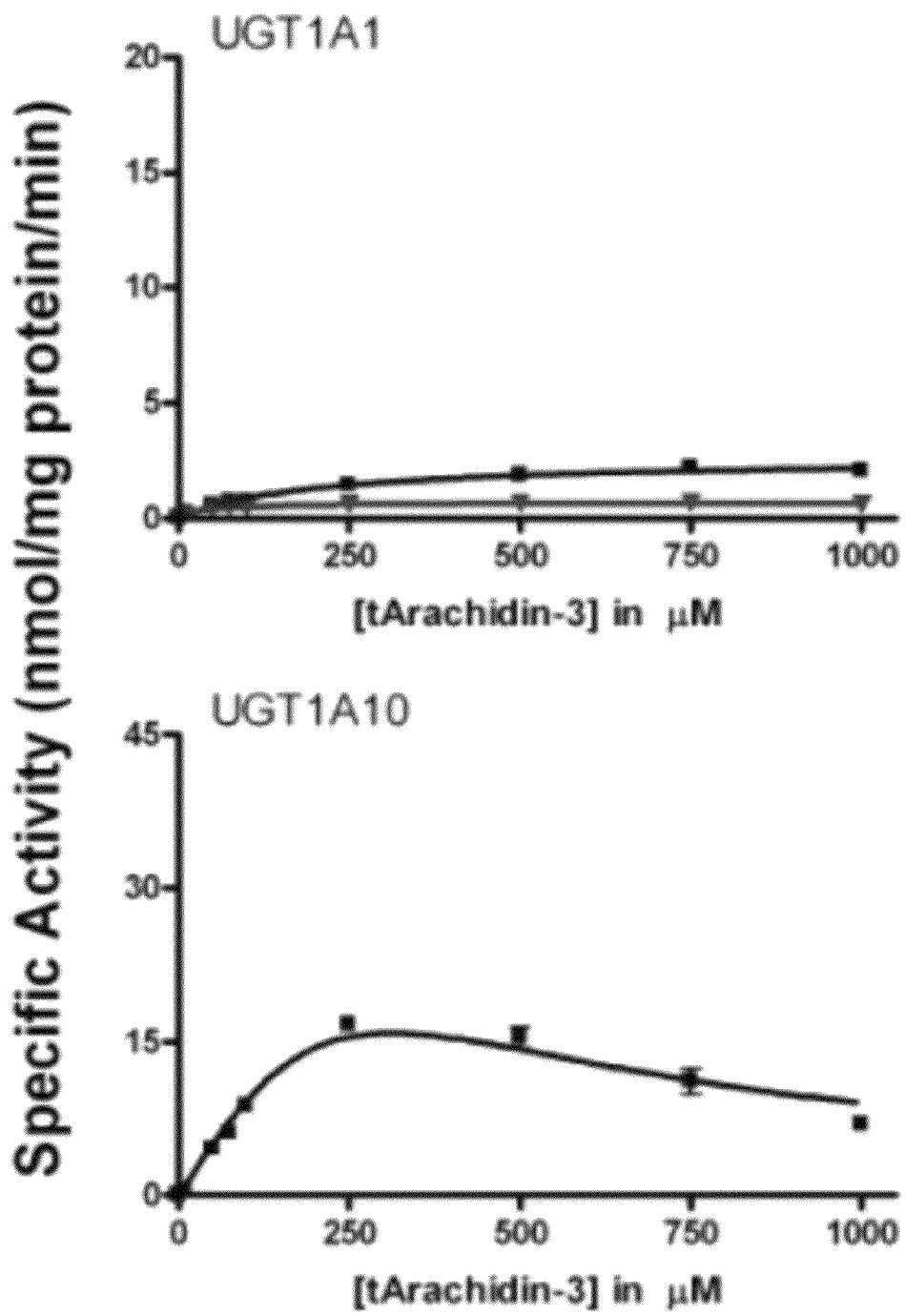

The present invention provides stilbenoid derivatives that have increased lipophilicity and/or increased negativity or hydrophilicity such that biological activity of the compound is altered relative to tRes. Accordingly, the stilbenoid derivatives may have increased in vivo bioavailability relative to tRes. The stilbenoid derivatives may additionally have increased half-lives compared to tRes. The present invention provides a method for increasing blood flow and microcirculation, wherein the method comprises administering a stilbenoid derivative to a subject. Also provided is a method for increasing blood flow and microcirculation in the kidneys during sepsis, wherein the method comprises administering a stilbenoid derivative to a subject experiencing sepsis. The present invention further provides a method for reducing the progression of acute kidney injury during sepsis, wherein the method comprises administering a stilbenoid derivative to a subject experiencing sepsis.

(I) Stilbenoid Derivatives (a) Compounds Comprising Formula (I)

One aspect of the present invention is the provision of stilbenoid derivatives. In general, a stilbenoid is a derivatized stilbene comprising at least one hydroxyl group. A derivatized stilbenoid, therefore, refers to a hydroxylated stilbene that is derivatized with at least one additional group. The stilbenoid derivative may be a monomer or an oligomer of a compound comprising Formula (I):

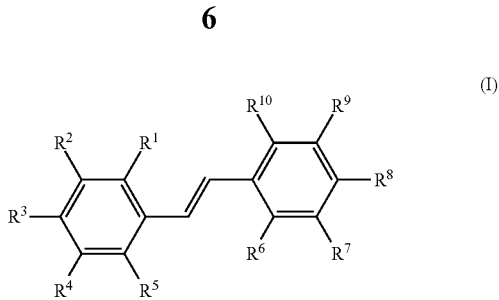

wherein:

$R^1$, $R^2$, $R^3$, $R^4$, $R^5$, $R^6$, $R^7$, $R^8$, $R^9$, and $R^{10}$ are independently chosen from hydrogen, hydroxyl, hydrocarbyl, substituted hydrocarbyl, hydrocarbyloxy, substituted hydrocarbyloxy, and sulfoxy; provided that at least one of the R groups is a hydroxyl or substituted hydroxyl group, and provided that if the compound comprising Formula (I) is monomeric, then the compound comprising Formula (I) is other than resveratrol.

In some embodiments, $R^1$, $R^2$, $R^3$, $R^4$, $R^5$, $R^6$, $R^7$, $R^8$, $R^9$, and $R^{10}$ are independently chosen from hydrogen, hydroxyl, alkyl, alkenyl, alkyoxy, alkenyloxy, aryloxy, glucuronidyloxy, glucosyloxy, and sulfoxy. Preferred alkenyl groups include isoprenyl (i.e., 3-methyl-1-butenyl), 3-methyl-but-2-enyl, and isopentadienyl. In further embodiments, $R^1$, $R^5$, $R^6$, $R^9$, and $R^{10}$ are hydrogen; $R^2$, $R^4$, $R^7$, and $R^8$ are chosen from hydrogen, hydroxyl, alkoxy, glucuronidyloxy, and sulfoxyl; and $R^3$ is chosen from hydrogen or alkenyl.

In one preferred embodiment, $R^1$, $R^3$, $R^5$, $R^6$, $R^7$, $R^9$, and $R^{10}$ are hydrogen; and $R^2$, $R^4$, and $R^8$ are independently chosen from hydroxyl, alkoxy, glucuronidyloxy, and sulfoxyl. In one iteration, for example, $R^2$, $R^4$, are methoxy and $R^8$ is hydroxyl. In another embodiment, $R^1$, $R^5$, $R^6$, $R^7$, $R^9$, and $R^{10}$ are hydrogen; $R^2$, $R^4$, and $R^8$ are independently chosen from hydroxyl, alkoxy, glucuronidyloxy, and sulfoxyl; and $R^3$ is alkenyl. In a further embodiment, $R^1$, $R^3$, $R^5$, $R^6$, $R^9$, and $R^{10}$ are hydrogen; $R^2$, $R^4$, and $R^8$ are independently chosen from hydroxyl, alkoxy, glucuronidyloxy, and sulfoxyl; and $R^7$ is alkenyl.

In still another embodiment, $R^1$, $R^3$, $R^5$, $R^6$, $R^9$, and $R^{10}$ are hydrogen; and $R^2$, $R^4$, $R^7$, and $R^8$ are independently chosen from hydroxyl, alkoxy, glucuronidyloxy, and sulfoxyl. In yet another embodiment, $R^1$, $R^5$, $R^6$, $R^9$, and $R^{10}$ are hydrogen; $R^2$, $R^4$, $R^7$, and $R^8$ are independently chosen from hydroxyl, alkoxy, glucuronidyloxy, and sulfoxyl; and $R^3$ is alkenyl.

In yet another embodiment, $R^1$, $R^3$, $R^5$, $R^6$, $R^7$, $R^8$, $R^9$, and $R^{10}$ are hydrogen; and $R^2$ and $R^4$ are independently chosen from hydroxyl, alkoxy, glucuronidyloxy, and sulfoxyl. In an alternate embodiment, $R^1$, $R^5$, $R^6$, $R^7$, $R^8$, $R^9$, and $R^{10}$ are hydrogen; $R^2$ and $R^4$ are independently chosen from hydroxyl, alkoxy, glucuronidyloxy, and sulfoxyl; and $R^3$ is alkenyl.

In some embodiments, the compounds comprising Formula (I) have increased an increased half-life over tRes. In some embodiments, the half-life of the compounds comprising Formula (I) may range from about 20 minutes to about 3 hours. In other aspects of the invention, the half-life of the compounds comprising Formula (I) may range between 30 minutes and 2 hours. In another aspect of the invention, the half-life may be greater than about 30 minutes, greater than about 45 minutes, or greater than about 1 hour.

(b) Compounds Comprising Formula (II)

In preferred embodiments, the stilbenoid derivative may be a monomer or an oligomer of a compound comprising Formula (II):

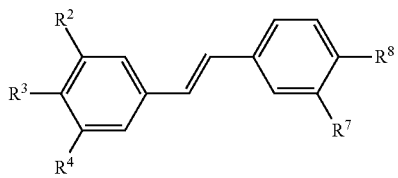

(II)

wherein:
$R^2$, $R^4$, and $R^8$ are independently chosen from hydroxyl, alkoxy, glucuronidyloxy, and sulfoxy;
$R^3$ is alkenyl; and
$R^7$ is chosen from hydrogen, hydroxyl, alkoxy, glucuronidyloxy, and sulfoxy Preferably, $R^2$ and $R^8$ are independently chosen from hydroxyl, alkoxy, and sulfoxy; $R^3$ is alkenyl; $R^4$ is glucuronidyloxy, and $R^7$ is chosen from hydrogen, hydroxyl, alkoxy, and sulfoxy.

In one embodiment, the compound comprising Formula (II) comprises Formula (IIa):

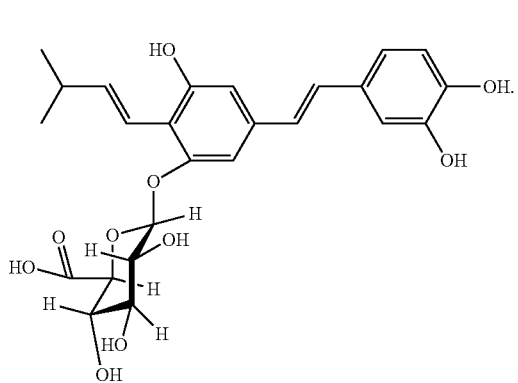

(IIa)

In another embodiment, the compound comprising Formula (II) comprises Formula (IIb):

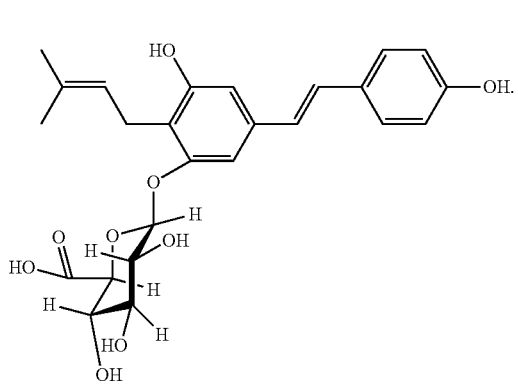

(IIb)

In a further embodiment, the compound comprising Formula (II) comprises Formula (IIc):

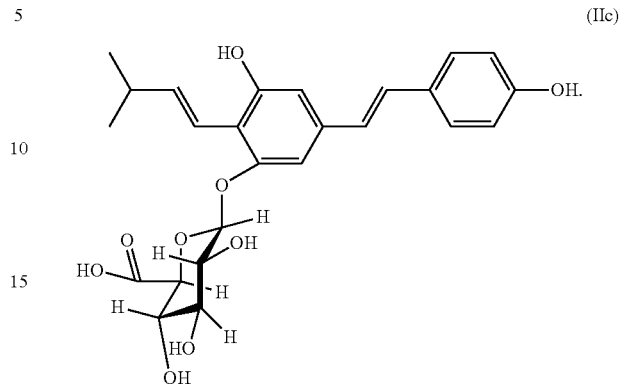

(IIc)

(c) Oligomers

Oligomers of any of the compounds described above in sections (I)(a) and (I)(b) may be dimers, trimers, tetramers, pentamers, hexamers, heptamers, and the like.

Those skilled in the art are familiar with the locations and linking groups that may link monomers of the compounds described above to form oligomers.

(d) Stereochemistry

Monomers of any of the compounds described above in sections (I)(a) and (I)(b) may be cis isomers or trans isomers. Preferentially, the monomers of the compounds detailed above are trans isomers.

Oligomers of any of the compounds described above in section (I)(c) may comprise cis isomers, trans isomers, or a combination of cis and trans isomers.

(e) Compositions Comprising a Compound Comprising Formula (II)

A further aspect of the invention encompasses a pharmaceutical composition comprising a compound comprising Formula (II), (IIa), (IIb), or (IIc) and at least one pharmaceutical excipient. Suitable compounds comprising Formula (II) are detailed above in section (I)(b).

(i) Excipients

Non-limiting examples of suitable excipients include diluents, binders, fillers, buffering agents, pH modifying agents, disintegrants, dispersing agents, stabilizers, preservatives, compaction agents, lubricants, coloring agents, and flavoring agents. The amount and types of excipients utilized to form the pharmaceutical composition may be selected according to known principles of pharmaceutical science.

In one embodiment, the excipient may include at least one diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lacitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

In another embodiment, the excipient may comprise a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, polypeptides, oligopeptides, and combinations thereof.

In another embodiment, the excipient may include a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may comprise a buffering agent. Representative examples of suitable buffering agents include, but are not limited to, MOPS, HEPES, TAPS, Bicine, Tricine, TES, PIPES, MES, Tris buffers or buffered saline salts (e.g., Tris buffered saline or phosphate buffered saline).

In various embodiments, the excipient may include a pH modifier. By way of non-limiting example, the pH modifying agent may be citric acid, sodium carbonate, or sodium bicarbonate.

In a further embodiment, the excipient may include a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Suitable effervescent disintegrants include sodium bicarbonate in combination with citric acid and sodium bicarbonate in combination with tartaric acid.

In another alternate embodiment, the excipient may also include a preservative. Non-limiting examples of suitable preservatives include antioxidants, such as alpha-tocopherol or ascorbate, and antimicrobials, such as parabens, chlorobutanol or phenol.

In yet another embodiment, the excipient may include a dispersion enhancer. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants.

In a further embodiment, the excipient may include a lubricant. Non-limiting examples of suitable lubricants include minerals such as talc or silica; and fats such as vegetable stearin, magnesium stearate or stearic acid.

In still another embodiment, it may be desirable to provide a coloring agent. Suitable color additives include, but are not limited to, food, drug and cosmetic colors (FD&C), drug and cosmetic colors (D&C), or external drug and cosmetic colors (Ext. D&C).

In a further embodiment, the excipient may include flavoring agents. Flavoring agents may be chosen from synthetic flavor oils and flavoring aromatics and/or natural oils, extracts from plants, leaves, flowers, fruits, and combinations thereof. By way of example, these may include cinnamon oils, oil of wintergreen, peppermint oils, clover oil, hay oil, anise oil, eucalyptus, vanilla, citrus oils (such as lemon oil, orange oil, grape and grapefruit oil), and fruit essences (such as apple, peach, pear, strawberry, raspberry, cherry, plum, pineapple, and apricot). In still another embodiment, the excipient may include a sweetener. By way of non-limiting example, the sweetener may be selected from glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; stevia-derived sweeteners; chloro derivatives of sucrose such as sucralose; sugar alcohols such as sorbitol, mannitol, sylitol, and the like. Also contemplated are hydrogenated starch hydrolysates and the synthetic sweetener 3,6-dihydro-6-methyl-1,2,3-oxathiazin-4-one-2,2-dioxide, particularly the potassium salt (acesulfame-K), and sodium and calcium salts thereof. In still another embodiment, the excipient may include a taste-masking agent. Taste-masking materials include cellulose hydroxypropyl ethers (HPC); low-substituted hydroxypropyl ethers (L-HPC); cellulose hydroxypropyl methyl ethers (HPMC); methylcellulose polymers and mixtures thereof; polyvinyl alcohol (PVA); hydroxyethylcelluloses; carboxymethylcelluloses and salts thereof; polyvinyl alcohol and polyethylene glycol co-polymers; monoglycerides or triglycerides; polyethylene glycols; acrylic polymers; mixtures of acrylic polymers with cellulose ethers; cellulose acetate phthalate; and combinations thereof.

The weight fraction of the excipient or combination of excipients in the composition may be about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

(ii) Exemplary Compositions

One exemplary composition comprises a compound comprising Formula (IIa) and at least one excipient. Another exemplary composition comprises a compound comprising Formula (IIb) and at least one excipient. A further exemplary composition comprises a compound comprising Formula (IIc) and at least one excipient.

(II) Methods for Preparing Stilbenoid Derivatives

The stilbenoid derivatives may be prepared by a variety of biological and/or chemical techniques. As detailed above in section (I), the stilbenoid or stilbenoid derivative may be monomeric or oligomeric. In some embodiments, stilbenoids, prenylated stilbenoids, and methoxylated stilbenoids may be produced using a hairy root culture system, such as that described in U.S. Pat. No. 7,666,677, the entire disclosure of which is incorporated herein by reference. For example, peanut hairy root cultures may be induced to produce stilbenoids and prenylated stilbenoids by contact with an elicitor such as sodium acetate, methyl jasmonate, or combinations thereof. The culture system may be a small reaction flask or it may be a large scale bioreactor. The stilbenoid may be purified from the culture medium and characterized using techniques known to persons skilled in the art.

In another embodiment, the stilbenoid may be isolated and purified from a plant that produces the stilbenoid or stilbenoid derivative of interest. In a further embodiment, the stilbenoid may be produced from microbial, plant, or animal cells engineered to express the enzymes involved in stilbenoid synthesis and/or derivatization. In yet another embodiment, the stilbenoid may be chemically synthesized from simpler precursor molecules.

The stilbenoid may be further derivatized using a variety of techniques. In some embodiments, the stilbenoid may be glucuronidated using a UDP-glucuronosyltransferase (UGT). Generally, the UGT will be a mammalian enzyme, and preferentially, a human liver UGT or human intestinal UGT. For example, the UGT may be within liver or intestinal cytosolic or microsomal preparations. Alternatively, the UGT may be purified from liver or intestinal cells. In other embodiments, the UGT may be a recombinant enzyme. The recombinant UGT may be expressed in a variety of cell types, including, for example, insect cells (such as Sf9 cells from *Spodoptera frugiperda* or S2 cells from *Drosophila melanogaster*), yeast cells (such as *Pichia, Saccharomyces,* or *Schizosaccharomyces*), microbial cells, animal cells, and the like. In an exemplary embodiment, a recombinant human UGT may be produced in baculovirus-infected Sf9 insect cells. The recombinant UGT may be purified from the cells and used in vitro. Alternatively, the recombinant UGT may be used in the expressing cells or in lysates of the expressing cells. Suitable human UGTs include UGT1A1, UGT1A3, UGT1A4, UGT1A5, UGT1A6, UGT1A7, UGT1A8, UGT1A9, UGT1A10, UGT2A1, UGT2A2, UGT2A3, UGT2B4, UGT2B7, UGT2B10, UGT2B11, UGT2B15, UGT2B17, UGT2B28, B3GAT1, B3GAT2, and B3GAT3.

In additional embodiments, the stilbenoid may undergo a sulfur transfer reaction catalyzed by a sulfotransferase (SULT). As detailed above for UGTS, the SULT may be a native liver or intestinal SULT enzymes or it may be a recombinant SULT enzyme. Suitable SULTs include SULT1A1, SULT1A2, SULT1A3, SULT1A4, SULT1B1, SULT1C2, SULT1C3, SULT1C4, SULT1D1P, SULT1E1, SULT2A1, SULT2B1, SULT4A1, and SULT6B1.

In still other embodiments, the stilbenoid may be contacted with suitable chemical reactants and optional catalysts to convert the stilbenoid into a derivatized stilbenoid. For example, the stilbenoid may be contacted with a methyl donor or a methylating agent such that a hydroxyl group is converted to a methoxy group. Similarly, the stilbenoid may be contacted with an alkyl donor or an alkylating agent to form a suitable derivative. Those of skill in the art will appreciate that a stilbenoid may undergo multiple derivatizations. For example, the stilbenoid may be prenylated and glucuronidated. In other case, the stilbenoid may be prenylated, glucuronidated, and sulfated. Alternatively, the stilbenoid may be prenylated and methylated.

(III) Method for Modulating Cannabinoid Receptor Activity

Another aspect of the invention encompasses a method for modulating activity of a cannabinoid receptor. The method comprises contacting the cannabinoid receptor with a monomer or oligomer of a compound comprising Formula (I), such that the activity of the cannabinoid receptor is modulated. Suitable examples of the compound comprising Formula (I) are detailed above in section (I)(a).

(a) Cannabinoid Receptor

Cannabinoid (CB) receptors are a class of G protein-coupled cell membrane receptors. Two subtypes of cannabinoid receptors, cannabinoid type 1 receptor (CB1) and cannabinoid type 2 receptor (CB2), have been characterized. The CB1 receptor is expressed mainly in the brain, but also in the lungs, liver and kidneys. The CB2 receptor is mainly expressed in the immune system and in hematopoietic cells. Evidence suggests that additional CB receptors may exist.

In an exemplary embodiment, the cannabinoid receptor may be a CB1 receptor. In another exemplary embodiment, the cannabinoid receptor may be a CB2 receptor. In yet another exemplary embodiment, the cannabinoid receptor may comprise both CB1 and CB2 receptors.

(i) In Vitro Cells

In some embodiments, the cannabinoid receptor may be within an isolated tissue, tissue homogenate, or fraction thereof. Suitable tissues that express endogenous cannabinoid receptors are listed above. In other embodiments, the cannabinoid receptor may be within an isolated cell or fraction thereof. Examples of cells that express endogenous cannabinoid receptors include neural cells, respiratory system cells, hepatic cells, renal cells, immune system cells (e.g., B cells, T cells, etc.), and hematopoietic cells.

Alternatively, the cell may express a recombinant cannabinoid receptor. Cells that may be engineered to express cannabinoid receptors include fungi or yeast, such as *Pichia, Saccharomyces,* or *Schizosaccharomyces*; insect cells, such as Sf9 cells from *Spodoptera frugiperda* or S2 cells from *Drosophila melanogaster*; and mammalian cell, such as mouse, rat, hamster, non-human primate, or human cells. When mammalian cell lines are used, the cell line may be any established cell line or a primary cell line that is not yet described. The cell line may be adherent or non-adherent, or the cell line may be grown under conditions that encourage adherent, non-adherent or organotypic growth using standard techniques known to individuals skilled in the art. Non-limiting examples of suitable mammalian cell lines include Chinese hamster ovary (CHO) cells, monkey kidney CVI line transformed by SV40 (COS7), human embryonic kidney line 293, baby hamster kidney cells (BHK), mouse sertoli cells (TM4), monkey kidney cells (CVI-76), African green monkey kidney cells (VERO), human cervical carcinoma cells (HeLa), canine kidney cells (MDCK), buffalo rat liver cells (BRL 3A), human lung cells (W138), human liver cells (Hep G2), mouse mammary tumor cells (MMT), rat hepatoma cells (HTC), HIH/3T3 cells, the human U2-OS osteosarcoma cell line, the human A549 cell line, the human K562 cell line, the human HEK293 cell lines, the human HEK293T cell line, and TRI cells. For an extensive list of mammalian cell lines, those of ordinary skill in the art may refer to the American Type Culture Collection catalog (ATCC®, Mamassas, Va.). In an exemplary embodiment, the cells engineered to express the cannabinoid receptor are CHO cells.

Cell fractions or extracts may be prepared from cells that naturally express cannabinoid receptors or from cells engineered to express recombinant cannabinoid receptors. Suitable cell extracts or fractions include cell lysates, membrane fractions, and microsomal fractions.

(ii) In Vivo Cells

In other embodiments, the cannabinoid receptor may be an endogenous cannabinoid receptor within a subject. Suitable subjects include, without limit, humans, as well as companion animals such as cats, dogs, rodents, and horses; research animals such as rabbits, sheep, pigs, dogs, primates, mice, rats and other rodents; agricultural animals such as cows, cattle, pigs, goats, sheep, horses, deer, chickens and other fowl; zoo animals; and primates such as chimpanzees, monkeys, and gorillas. In a preferred embodiment, the subject may be a human.

(b) Contacting the Cannabinoid Receptor

The method of the invention comprises contacting the cannabinoid receptor with a monomer or oligomer of a compound comprising Formula (I). In embodiments in which the cannabinoid receptor is in vitro, the cell or fraction thereof may be contacted with the compound comprising Formula (I) by incubating the cell or fraction thereof with the compound. Thus, the cell or fraction thereof may be contacted with a buffer or a culture medium containing the compound comprising Formula (I).

In embodiments in which cannabinoid receptor is in vivo, the compound comprising Formula (I) may be administered to the subject by a variety of routes. For example, a composition comprising the compound comprising Formula (I) may be administered orally (via a solid or liquid dosage form), parenterally (i.e., subcutaneously, intradermally, intravenously, intramuscularly, intracranially, or intraperitoneally), or topically (i.e., transdermally or transmucosally).

The amount of the compound comprising Formula (I) contacted with the cannabinoid receptor can and will vary depending upon the mode of contact, the chemical identity of the compound comprising Formula (I), and so forth. Those of skill in the art are familiar with methods for determining the appropriate amount.

(c) Modulation of Cannabinoid Receptor Activity

Contact with the compound comprising Formula (I) modulates the activity of the cannabinoid receptor. Without being bound to any particular theory, it is believed that the compound comprising Formula (I) has affinity for the cannabinoid receptor and binds to a binding site of the cannabinoid receptor. The affinity ($K_i$) of the compound comprising Formula (I) may be less than about 200 μM, less than about 50 μM, less than about 20 μM, less than about 5 μM, less than about 1 μM, less than about 0.1 μM, less than about 50 nM, less than about 10 nM, or less than about 1 nM.

In some embodiments, the compound comprising Formula (I) may fully activate the cannabinoid receptor and, thus, function as an agonist. In other embodiments, the compound comprising Formula (I) may partially activate the cannabinoid receptor and, thus, function as a partial agonist. In additional embodiments, the compound comprising Formula (I) may inhibit the cannabinoid receptor and, thus, function as an inverse agonist. In further embodiments, the compound comprising Formula (I) may block the action of cannabinoid receptor agonists and, thus, function as an antagonist. In an alternate embodiment, various derivatives of the compound comprising Formula (I) may be involved in modulating the cannabinoid receptor.

Modulation of cannabinoid receptors in vivo may be used to treat a variety of conditions. As used herein, the terms "treat" or "treating" refer to preventing or delaying the onset of the condition; inhibiting or alleviating the symptoms associated with the condition; or slowing, inhibiting, or reversing the progression of the condition. Non-limiting examples of suitable conditions include obesity, drug dependence, inflammation, pain, cardiovascular conditions, cancer, neurodegenerative disorders, and age-related disorders.

(IV) Method for Preventing Cell Damage by Reactive Nitrogen Species

Yet another aspect of the invention provides a method for preventing damage by a reactive nitrogen species in a cell. The method comprises comprising contacting the cell with a monomer or oligomer of a compound comprising Formula (I) such that the reactive nitrogen species is scavenged by the compound comprising Formula (I) and the cell is protected from damage from the reactive nitrogen species. Suitable examples of the compound comprising Formula (I) are detailed above in section (I)(a).

(a) Reactive Nitrogen Species

A variety of reactive nitrogen species may be scavenged by the compound comprising Formula (I). In one embodiment, the reactive nitrogen species may be peroxynitrite ($ONOO^-$). In another embodiment, the reactive nitrogen species may be nitric oxide (NO). In still another embodiment, the reactive nitrogen species may be nitrogen dioxide ($NO_2$). In a further embodiment, the reactive nitrogen species may be dinitrogen trioxide ($N_2O_3$). In yet another embodiment, the cell may comprise a combination of reactive nitrogen species.

(b) Contacting the Cell with a Compound Comprising Formula (I)

In some embodiments, the cell may be an isolated cell. Non-limiting examples of suitable in vitro cells and means of contacting the cell with the compound comprising Formula (I) are presented above in sections (III)(a)(i) and (III)(b), respectively. In other embodiments, the cell may be in vivo, i.e., within a subject. Suitable subjects and means of contacting the cell with the compound comprising Formula (I) are detailed above in sections (III)(a)(ii) and (III)(b), respectively. Non-limiting examples of suitable in vivo cells include renal, hepatic, neural, cardiac, vasculature, blood, epithelial, endocrine, immune, respiratory, gastric, intestinal, urogenital, muscle, and bone cells. In a preferred embodiment, the cell may be a renal cell. In an exemplary embodiment, the cell may be a renal cell and contact with the compound comprising Formula (I) may protect the renal cells from sepsis-induced damage.

Upon contact of the cell with the compound comprising Formula (I), the compound may bind to or scavenge the reactive nitrogen species or combination thereof. Binding or scavenging of the reactive nitrogen species essentially sequesters the reactive nitrogen species such that the reactive nitrogen species is unable to react with (e.g., oxidize, nitrate, etc.), modify, or damage cellular proteins or other molecules. Various derivatives of the compound comprising Formula (I) may be involved in scavenging reactive nitrogen species.

(V) Method for Improving Blood Flow and Microcirculation

Yet another aspect of the invention provides a method for improving blood flow and microcirculation in a subject through vasodilatation. The method comprises comprising administering a monomer or oligomer of a compound comprising Formula (I) to a subject such that the blood flow and microcirculation in the subject are enhanced. Suitable examples of the compound comprising Formula (I) are detailed above in section (I)(a). Various derivatives of the compound comprising Formula (I) may be involved in enhancement of blood flow and microcirculation.

Without being bound by any particular theory, it is believed that administration of a monomer or oligomer of a compound comprising Formula (I) may improve blood flow and microcirculation by reducing vascular resistance.

(a) Administration of a Compound Comprising Formula (I)

Administration of a compound comprising Formula (I) may be provided to a subject through various means. Suitable subjects include, without limit, humans, as well as companion animals such as cats, dogs, rodents, and horses; research animals such as rabbits, sheep, pigs, dogs, primates, mice, rats, and other rodents; agricultural animals such as cows, pigs, goats, sheep, horses, deer, chicken and other fowl; zoo animals; and primates such as chimpanzees, monkeys and gorillas. In a preferred embodiment, the subject may be human.

Administration of a compound comprising Formula (I) may be accomplished by local administration, by oral administration (via solid or liquid dosage form), parenterally (i.e., subcutaneously, intradermally, intravenously, intramuscularly, intraperitoneally, or topically (transdermally or transmucosally).

The amount of the compound comprising Formula (I) administered to the subject can and will vary depending on the mode of contact, the chemical identity of the compound comprising Formula (I), and so forth. In some embodiments, the dosage may vary from about 1 mg to about 30 mg of the compound of Formula (I) per kilogram of the subject and may be dosed from one to four times in a period of 48 hours. In another embodiment, the dosage may vary from about 10 mg to about 30 mg of the compound of Formula (I) per kilogram of the subject and may be dosed from one to four times in a period of 48 hours. In another embodiment, the dosage may be about 10 mg of the compound of Formula (I) per kilogram of the subject, dosed every six hours for 18 hours.

The method of increasing blood flow and microcirculation may be used to treat a variety of conditions. As used herein, the terms "treat" or "treating" refer to preventing or delaying the onset of the condition; inhibiting, or alleviating the symptoms associated with the condition; or slowing inhibiting, or reversing the condition.

(VI) Methods for Improving Renal Blood Flow and Microcirculation and/or Preventing Progression of Acute Kidney Injury During Sepsis Yet another aspect of the invention provides a method for improving renal blood flow and microcirculation in a subject during sepsis. The method comprises comprising administering a monomer or oligomer of a compound comprising Formula (I) or a derivative thereof to a subject experiencing sepsis such that the renal blood flow and microcirculation in the subject is enhanced. Suitable examples of the compound comprising Formula (I) are detailed above in section (I)(a). Various derivatives of the compound comprising Formula (I) may be involved in enhancement of renal blood flow and microcirculation.

(a) Septic Conditions

Sepsis is a disseminated inflammatory response caused by a microbial infection and is a major cause of death among critically ill patients. Sepsis and septic shock may result in a number of effects on a subject. Sepsis may impede nutrients and oxygen from reaching organs, causing tissue damage and ultimately organ failure. Circulation and microcirculation may be decreased, which may lead to excess production of reactive nitrogen species (RNS). Moreover, septic shock can lead to a reduction in blood pressure, causing further hypoxia. These effects may also be seen in the kidneys where sepsis can lead to Acute Kidney Injury (AKI). AKI is characterized by damage to the renal tissue, and increases the incidence of mortality with sepsis to near 75%. Progression of AKI during sepsis is a result of both reduced circulation and the resulting generation of RNS. Reactive nitrogen species are thought to be key for progression of AKI as they may cause oxidative damage such as protein nitration, mitochondrial dysfunction, and DNA damage.

(b) Administration of a Compound Comprising Formula (I)

Administration of the compound comprising of Formula (I) for the treatment of sepsis may be accomplished by the methods described in section (V)(a). After the onset of septic conditions, the compound comprising Formula (I) may be administered to a subject in the dosages described in section (V)(a).

(c) Methods of Action of the Compound Comprising Formula (I) on Sepsis

Without being bound to a particular theory, there may be multiple modes of action of the compound comprising Formula (I) for the treatment of sepsis. As described in section (IV), compounds comprising Formula (I) may scavenge RNS. Administration of the compound of Formula (I) to a subject for the treatment of sepsis may lower the amount of RNS in the kidney, which may curb oxidative damage during sepsis.

Moreover, the compounds comprising Formula (I) may act to increase blood flow as well as microcirculation in the kidneys through a decrease in vascular resistance. Increased blood flow to the kidneys may inhibit further RNS production, which may result in less damage to the kidneys due to the oxidation effects of RNS. Moreover, increased blood flow may enhance oxygen and nutrient flow to the kidneys, preventing further tissue damage. Because AKI is one of the main causes of mortality in sepsis, inhibition of the progression of AKI can lead to higher survival rates for sepsis.

DEFINITIONS

To facilitate understanding of the invention, the following terms are defined.

The term "acyl," as used herein alone or as part of another group, denotes the moiety formed by removal of the hydroxy group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl or substituted hydrocarbyl.

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups having at least one carbon-carbon double bond that preferably contain from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups having at least one carbon-carbon triple bond that preferably contain from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic aromatic groups. These aromatic groups are preferably monocyclic, bicyclic, or tricyclic groups containing from 6 to 14 atoms in the ring portion. The term "aromatic" encompasses the "aryl" and "heteroaryl" groups defined below.

The term "aryl" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" or "halo" as used herein alone or as part of another group refer to chlorine, bromine, fluorine, and iodine.

The term "heteroaryl" embraces unsaturated heterocyclyl radicals. Examples of unsaturated heterocyclyl radicals, also termed "heteroaryl" radicals include unsaturated 3 to 8 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 8-membered heteromonocyclic group containing an oxygen atom, for example, pyranyl, furyl, etc.; unsaturated 3 to 8-membered heteromonocyclic group containing a sulfur atom, for example, thienyl, etc.; unsaturated 3- to 8-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 8-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like. The term also embraces radicals where heterocyclyl radicals are fused with aryl radicals or a non-aromatic cyclic system. Examples of such fused bicyclic radicals include benzofuran, benzothiophene, and the like.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described below. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

The term "hydrocarbyl" as used herein describes organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The terms "substituted hydrocarbyl," "substituted alkyl," "substituted alkenyl," and "substituted aryl," as used herein refer to hydrocarbyl, alkyl, alkenyl, and aryl moieties, respectively, that are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, aryloxy, hydroxy, protected hydroxy, acyl, acyloxy, nitro, amino, amido, nitro, cyano, ketals, acetals, esters and ethers.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples demonstrate various aspects of the invention.

Example 1

Glucuronidation of Resveratrol Analogs

The following example was designed to examine the glucuronidation of trans-resveratrol (tRes), trans-arachidin-1 (tA1), trans-arachidin-3 (tA3), and trans-piceatannol (tPice). Eight human recombinant UGT1A isoforms (UGT1A1, 1A3, 1A4, 1A6, 1A7, 1A8, 1A9, and 1A10; 5 µg) expressed as His-tag proteins in baculovirus-infected Sf9 insect cells and human liver microsomes (from one donor; HL2; 50 µg) and human intestinal microsomes (from two donors; HI36 and HI41; 50 µg) were evaluated for their ability to glucuronidate these four compounds. The concentrations of the substrate and co-substrate (i.e., UDP-GlcUA) were 250 µM and 4 mM, respectively. Glucuronidation products were analyzed by HPLC and LCMS/MS.

As shown in FIG. 1, unique product profiles were seen for each enzyme source with the major isoforms involved in each being predominantly hepatic UGT1A1 and UGT1A9 and extrahepatic UGT1A7 and UGT1A10. The production of a large amount to tA1-3G* by HIM suggests another isoform, possibly from the UGT2B family, is involved in the metabolism of this compound. tRes was glucuronidated to 3-O— and 4'-O-Glucs by both hepatic UGT1A1 and extrahepatic UGT1A10. The presence of an additional 3'-OH group on the B ring (i.e., phenol ring) of tRes in tPice decreased the formation of the 3-O-Gluc by UGT1A1 however the 4'-O-Gluc is still efficiently produced by UGT1A10. The presence of a prenyl group on ring A (tA3) resulted in significant inhibition of 3-O-glucuronidation by UGT1A1 and UGT1A10. The addition of a prenyl group and a hydroxyl group (tA1) completely blocked formation of any Gluc by UGT1A1, as well as the formation of the 3-O-Gluc by UGT1A10.

The kinetic constants of the glucuronidation reactions using recombinant human UGT1A1 and UGT1A10 were determined by measuring the enzyme activity in the presence of increasing concentrations of substrate (see FIG. 2). The 4'-O-Gluc products of tA1 and 1A3 by UGT1A10 exhibited substrate inhibition kinetics. Table 1 presents the kinetic constants.

TABLE 1

| Kinetic Constants | | | | | | | |
|---|---|---|---|---|---|---|---|
| Enzyme | Substrate | Product | Kinetics | $V_{max}$ (µM) | $K_m$ (nmol/mg protein/min) | $V_{max}/K_m$ | n (Hill coeff) |
| UGT1A1 | tRes | tRes-4'G | Hill | 1.3 ± 0.05 | 25.3 ± 4.8 | 0.44 | 2.2 |
|  |  | tRes-3G | M-M | 30.9 ± 2.0 | 705 ± 89 | 0.50 |  |
|  | tPice | tPice-4'G* | M-M | 2.8 ± 0.4 | 50.8 ± 16 | 0.54 |  |
|  |  | tPice-3G* | M-M | 13.5 ± 3.8 | 172 ± 67 | 0.78 |  |
|  | tA1 | tA1-4'G* | -- | -- | -- | -- | -- |
|  |  | tA1-3G* | -- | -- | -- | -- | -- |

TABLE 1-continued

Kinetic Constants

| Enzyme | Substrate | Product | Kinetics | $V_{max}$ (μM) | $K_m$ (nmol/mg protein/min) | $V_{max}/K_m$ | n (Hill coeff) |
|---|---|---|---|---|---|---|---|
| | tA3 | tA3-4'G* | M-M | 2.6 ± 0.1 | 196 ± 24 | 0.01 | |
| | | tA3-3G* | M-M | 0.67 ± 0.02 | 32.9 ± 5.2 | 0.02 | |
| UGT1A10 | tRes | tRes-4'G | Hill | 55.8 ± 4.6 | 375 ± 62 | 0.14 | 1.2 |
| | | tRes-3G | M-M | 4.6 ± 0.3 | 347 ± 63 | 0.13 | |
| | tPice | tPice-4'G* | Hill | 38.9 ± 4.2 | 36.6 ± 6.1 | | 1.7 |
| | | tPice-3G* | M-M | 7.0 ± 2.5 | 133 ± 72 | 0.05 | |
| | tA1 | tA1-4'G* | USI | ** | ** | ** | |
| | | tA1-3G* | -- | -- | -- | -- | |
| | tA3 | tA3-4'G* | USI | ** | ** | ** | |
| | | tA3-3G* | -- | -- | -- | -- | |

-- No activity
** Atypical kinetics profiles make it difficult to predict kinetic values.

Example 2

Molecular Modeling of Cannabinoid Receptor Binding

There have been limited efforts reported in the literature to predict the activity and selectivity of cannabinoid receptor antagonists and agonists. Most of the computational efforts for cannabinoids have used 3D-QSAR modeling (CoMFA and/or CoMSIA), which requires alignment of 3D-conformations for ligands. Because of this limitation, 3D-QSAR analyses, which generally are applied only to a set of compounds with common backbone and are not appropriate for simultaneous modeling of multiple classes of compounds, cannot be expected to be helpful for the prediction of the activity of novel classes of compounds.

To deal with the limitations of existing molecular models, therefore, activity and selectivity models for CB1 antagonists and CB2 agonists were prepared. These models are based on multiple chemical classes of reported CB receptor ligands, using support vector machines, and pharmacophore models, which summarize the arrangement of physicochemical functional groups needed for binding to CB1 and CB2.

Figure 3A:
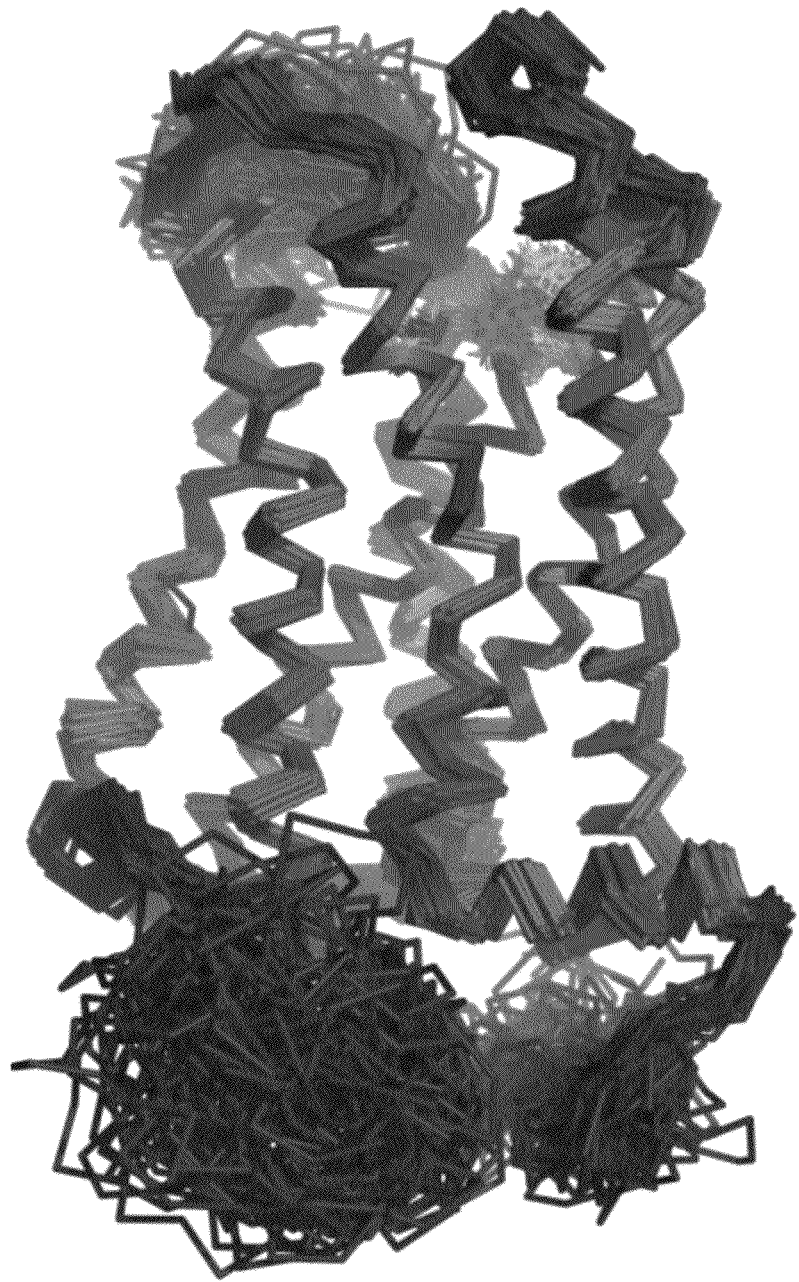
FIG. 3 illustrates molecular modeling of cannabinoid subtype 2 (CB2) receptor. (A) Conformational diversity observed in models generated using Modeller, represented by superposition of 132 CB2 structures. (B) Putative binding pose of tA2 bound to CB2 receptor model. (C) Putative binding pose of N-alkylisatinhydrazine (CB2 inverse agonist, $IC_{50}$: 131 nM) bound to CB2 receptor model.

Multiple models of CB2 were prepared using an extensively optimized protocol for docking and enrichment of CB2 agonists involving docking several ligands on >100 models of CB2 receptors built using Modeller, based on a bovine rhodopsin X-ray structure. Since evidence has been reported of the particular importance of K109 and S285 for binding of CB2 ligands, S285 was selected as a central point for docking. The resulting models were found to have a considerable degree of difference in side-chain and backbone conformation (FIG. 3A).

From the docking results, poses were selected for which the common structure of docked ligands showed minimum root mean squared deviation (RMSD) and the predicted activities showed maximum correlation coefficients with experimentally estimated $pIC_{50}/pK_i$. After this initial selection followed by energy minimization, models that performed well in a small scale enrichment study, were tested and also found to perform efficiently in a large scale enrichment study, retrieving known CB2 ligands (14-85% of the training set CB2 ligands in the top 1% of predicted CB2 hits) from a huge pool of decoys (~229,000).

Figure 3B:
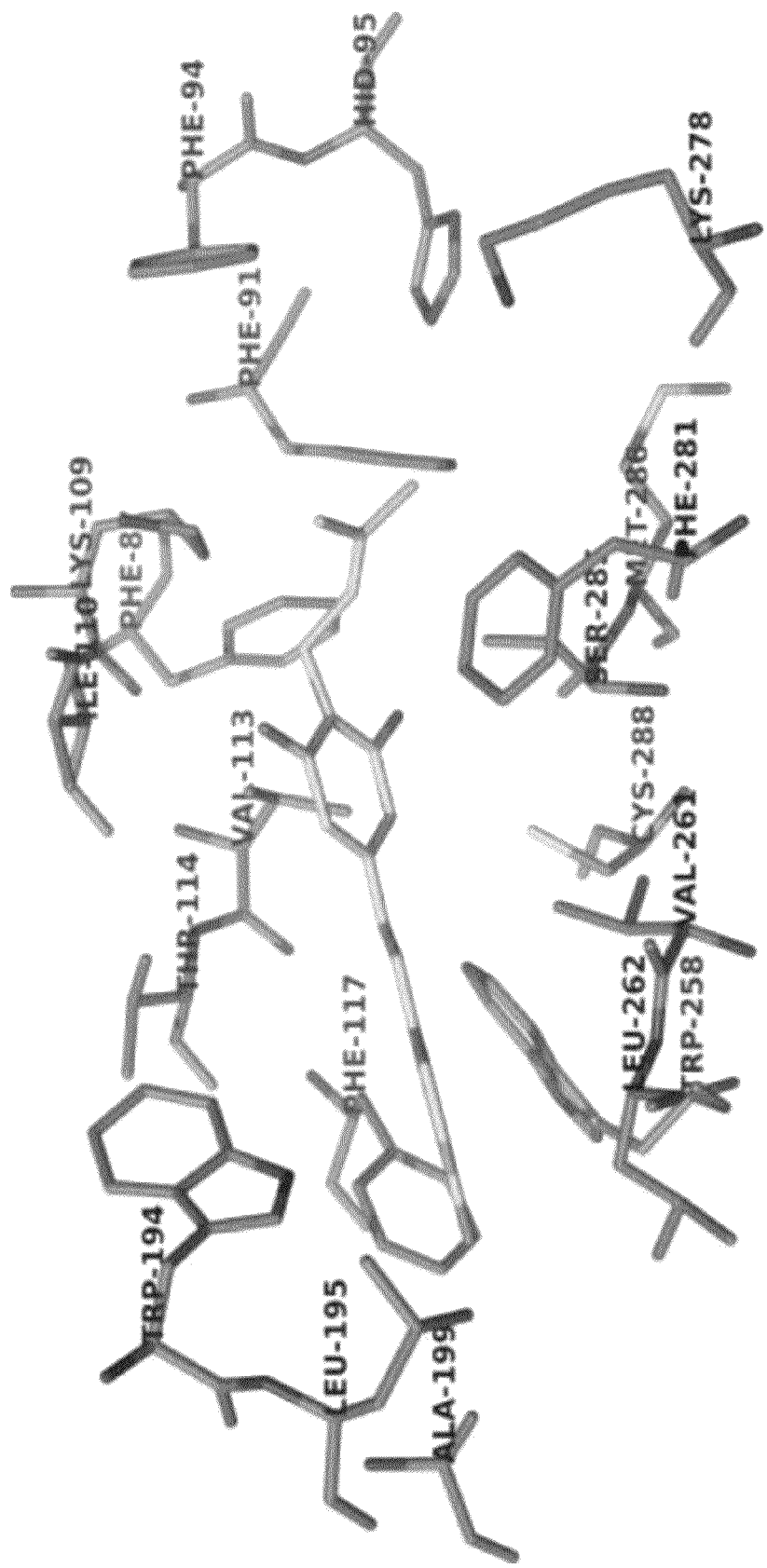
Figure 3C:
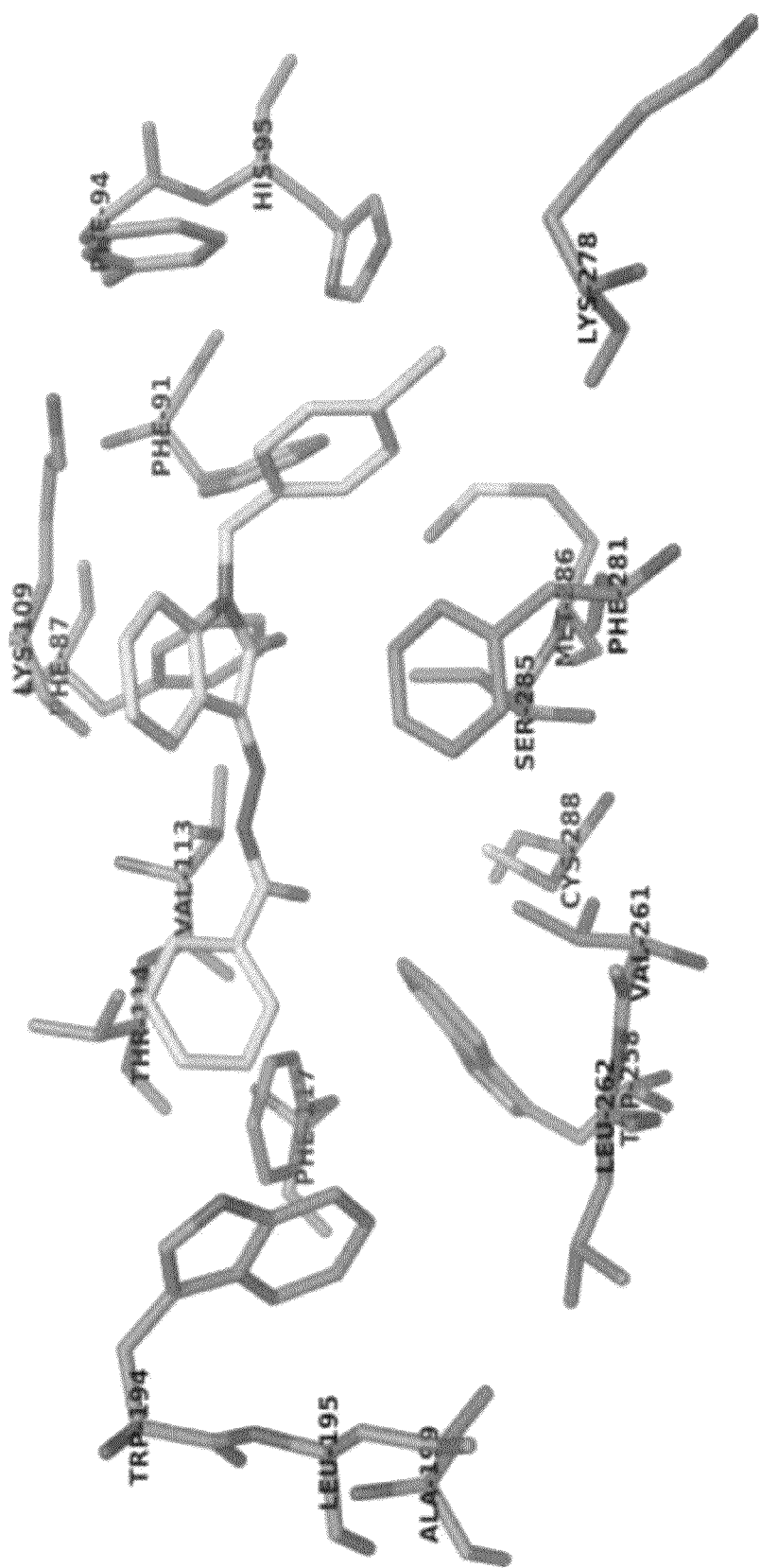

Basic docking of tRes-like ligands on 132 models of CB2 were performed. The selected best model, which showed low RMSD among the docked ligands and passed visual inspection, was used to rationalize observed difference in binding of 5 ligands (tRes, tPice, tA1, tA2, tA3). In the docked poses, these ligands interact with three regions of CB2, forming a hydrogen bond with S285 and hydrophobic interactions with two pockets, one formed by F87, F91, F281, K109, M286 and another formed by F117, W258, W194 and 1198 (see FIG. 3B). The B ring (i.e., phenol ring) orients into the former hydrophobic pocket, while the A ring orients into the latter hydrophobic pocket. Either a 3-OH or 5-OH group forms a hydrogen bond with S285. The isoprenyl moiety of the arachidins improves the predicted binding, while increases in hydrophilicity of the phenol ring (additional OH groups), which interacts with a hydrophobic pocket, reduces the predicted binding. Table 2 presents Glide G scores (more negative corresponds to higher affinity) of the tRes analogs.

TABLE 2

Glide Scores and $K_i$ Values for CB2.

| Ligand | GScore | $K_i$ (μM) |
|---|---|---|
| 3-Gluc-tA3 | −7.51 | — |
| tA2 | −7.48 | — |
| tA3 | −7.11 | 11.3 ± 0.6 |
| 3-Gluc-tA2 | −7.00 | — |
| tA1 | −6.95 | 12.6 ± 1.7 |
| 3-Gluc-tA1 | −6.88 | — |
| tRes | −6.66 | 65.5 ± 12 |
| tPice | −6.27 | 114 ± 7.8 |
| 4'-Gluc-tPice | −6.03 | — |
| 3-Gluc-tRes | −5.95 | — |
| 3-Gluc-tPice | −5.86 | >100 |
| 4'-Gluc-rRes | −5.71 | >100 |

Example 3

Cannabinoid Receptor Binding Studies

Figure 4:
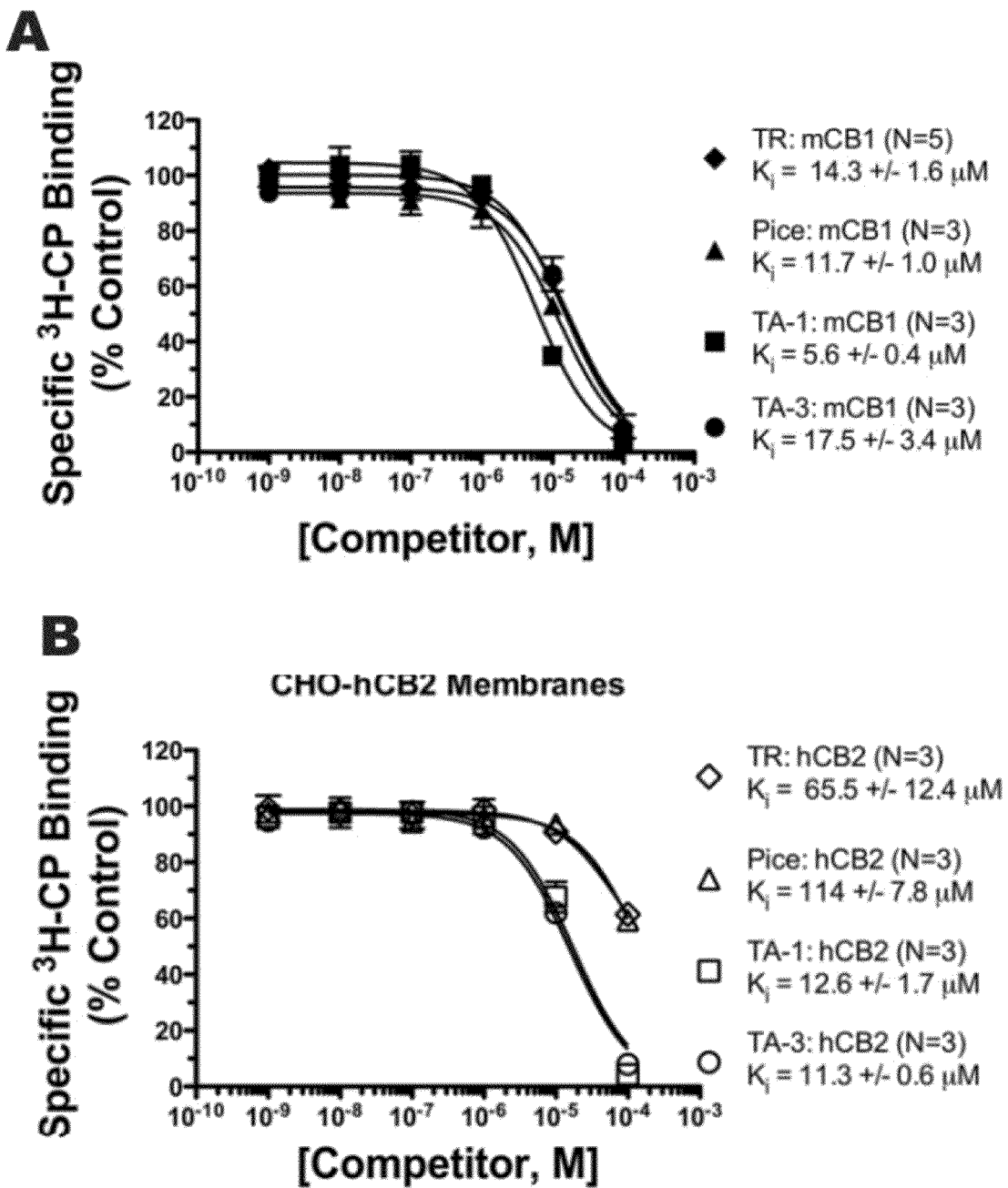
FIG. 4 presents binding curves and affinities of tRes and analogs for cannabinoid receptors. Plotted is the percent of control $^3$H—CB binding in the presence of increasing concentrations of tRes (TR), tPice (Pice), tA1 (TA-1), and tA3 (TA-3) in mouse brain-mCB1 membranes (A) and CHO-hCB2 membranes (B).

To determine the binding affinity of tRes and its analogs to CB receptors, in vitro binding studies were performed. Membrane preparations were prepared from mouse brain to examine CB1 binding. For CB2 binding, membrane preparations were prepared from CHO cells stably transformed with human CB2. Membranes were incubated with 0.2 nM $^3$H—CP (i.e., CP 55,940, a CB1 agonist) and increasing concentrations of tRes, tPice, tA1, or tA3 for 90 min at room temperature, and then filtered.

tRes and all analogs bound to CB1 receptors with affinities (K) in the low 5-20 μM range (FIG. 4, upper). The rank order for CB1 was tA1>tPice>tRes=tA3. Although tA1 and tA3 also bound to CB2 with similar affinities as CB1 (FIG. 4, lower), tRes and tPice had 6- to 10-fold lower affinities for CB2 than that observed for CB1.

In addition, all compounds except for tA3 exhibited approximately 2- to 10-fold selectively for binding to CB1 relative to CB2. Based on these observations, it appears that addition of the isoprenyl group, found only in tA1 and tA3, significantly enhances the binding affinity of these analogs for CB2 by approximately 6-10-fold. Furthermore, combination of the isoprenyl group and an additional hydroxyl group in tA1 apparently also modestly enhanced the binding affinity of this analog for CB1 by 2-fold. In summary, these studies clearly establish that tRes and several structurally related analogs bind to both CB1 and CB2 receptors with a low µM affinity. Most importantly, observations that minor modifications to the basic tRes structure resulted in marked alterations in the affinity of various analogs for CB receptors, indicate that tRes likely represents a useful scaffold for future design of selective and efficacious CB1 and CB2 ligands.

Table 2, above, also presents the $K_i$ values for CB2. There is an excellent correlation between the predicted values (G-scores) and the observed K values.

Example 4

Reactive Nitrogen Species Scavenging

Reactive nitrogen species (NRS) play important roles in many of the diseases and conditions reported to be ameliorated by tRes. To examine this in more detail, a RNS scavenging assay was developed. The assay uses nitration of bovine serum albumin (BSA) and oxidation of glutathione (GSH) to monitor two biologically relevant toxic consequences of $ONOO^-$ production: protein nitration and thiol oxidation. Accordingly, BSA was incubated with authentic $ONOO^-$ in the presence of varying concentrations of tRes. The scavenging activity of tRes was compared to that of N-acetylcysteine (NAC).

Figure 5:
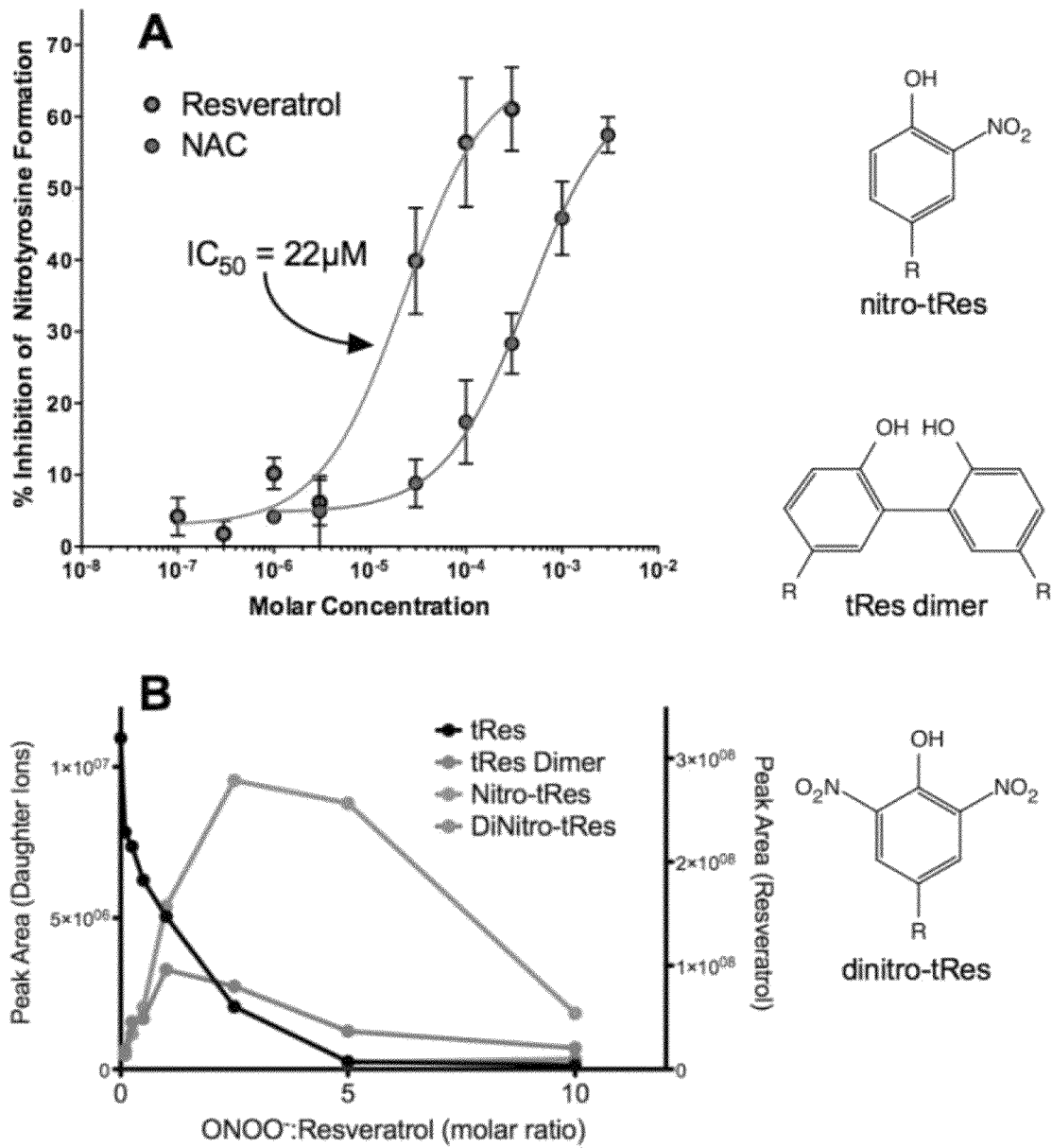
FIG. 5 depicts reactive nitrogen species (RNS) scavenging activity of tRes. (A) Plotted is the percent inhibition of protein nitration by tRes and N-acetylcysteine (NAC). (B) LC/MS/MS analysis of daughter ions identified nitro and tRes dimmers produced as tRes was consumed. Dinitro-tRes appeared at higher ONOO⁻:tRes ratios.

It was found that tRes inhibited nitration with an $IC_{50}$ of about 22 µM (see FIG. 5A). tRes was about 20-fold more potent than the known $ONOO^-$ scavenger NAC. Moreover, reacting tRes with authentic $ONOO^-$ or the $ONOO^-$ generator SIN-1 resulted in nitrated tRes and tRes dimers identified by LC/MS/MS (see FIG. 5B).

Example 5

Effect of tRes on Murine Model of Sepsis

Figure 6:
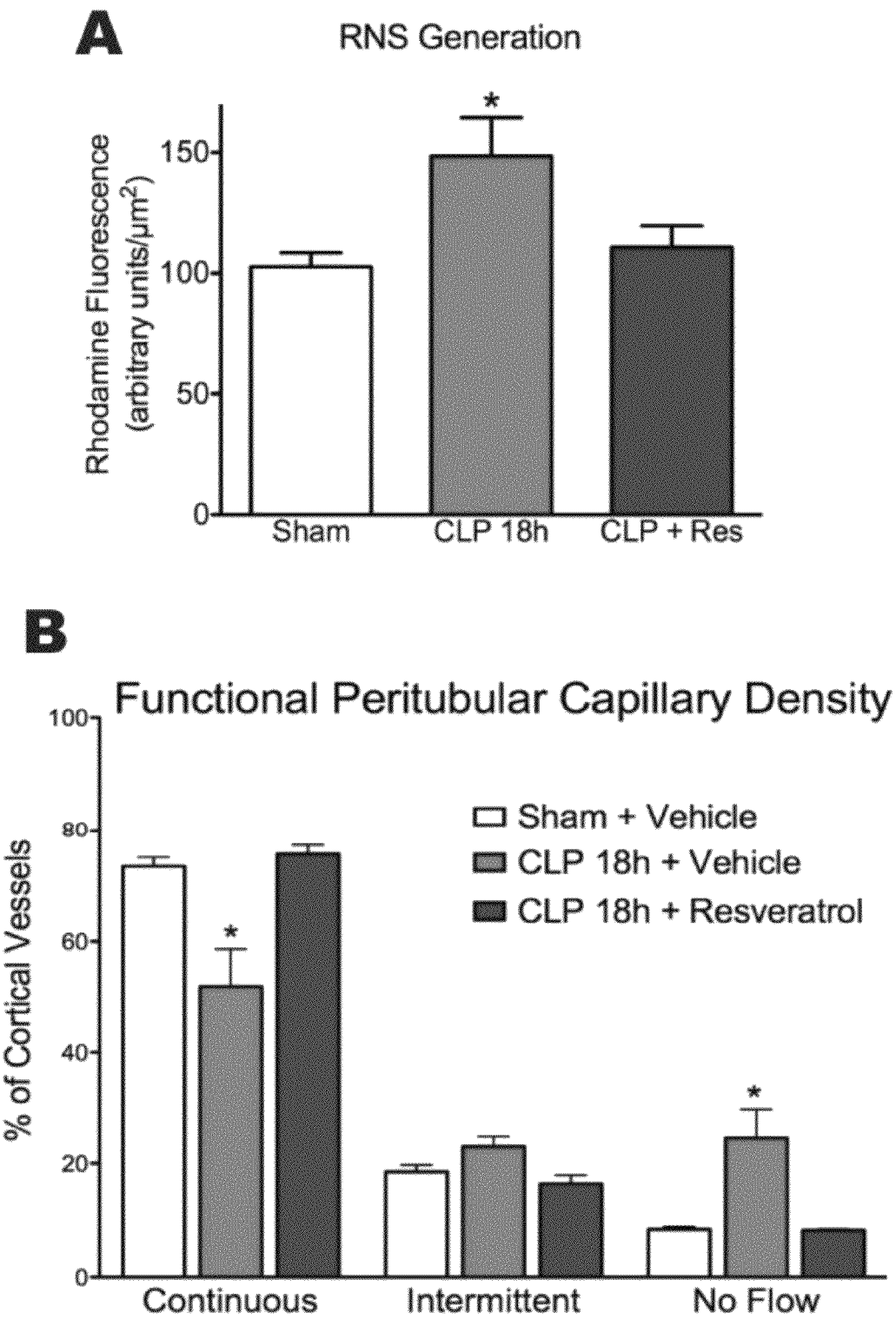
FIG. 6 shows the effect of tRes on a murine model of sepsis. (A) presents RNS generation in each treatment group. (B) presents the functional peritubular capillary density in each group. * $P<0.05$ compared to sham.

An established murine cecal ligation and puncture model (CLP) of sepsis-induced renal injury (Wu et al., J. Am. Soc. Nephrol., 2007, 18:1807-1815) was used to assess potency and efficacy of tRes. tRes (30 mg/kg) was administered by i.p. 30 min prior to and 6 hr post CLP. Control (sham) mice underwent surgery but not CLP. Each treatment group contained 4-5 mice. Renal $ONOO^-$ generation (rhodamine fluorescence) and renal peritubular capillary perfusion were quantified using intravital video microscopy (IVVM) on anesthetized mice in each of the treatment groups. At 18 hr post CLP, tRes blocked RNS generation in the kidney and preserved renal capillary perfusion (see FIG. 6).

Example 6

Inhibition of G-Protein Activity

Figure 7:
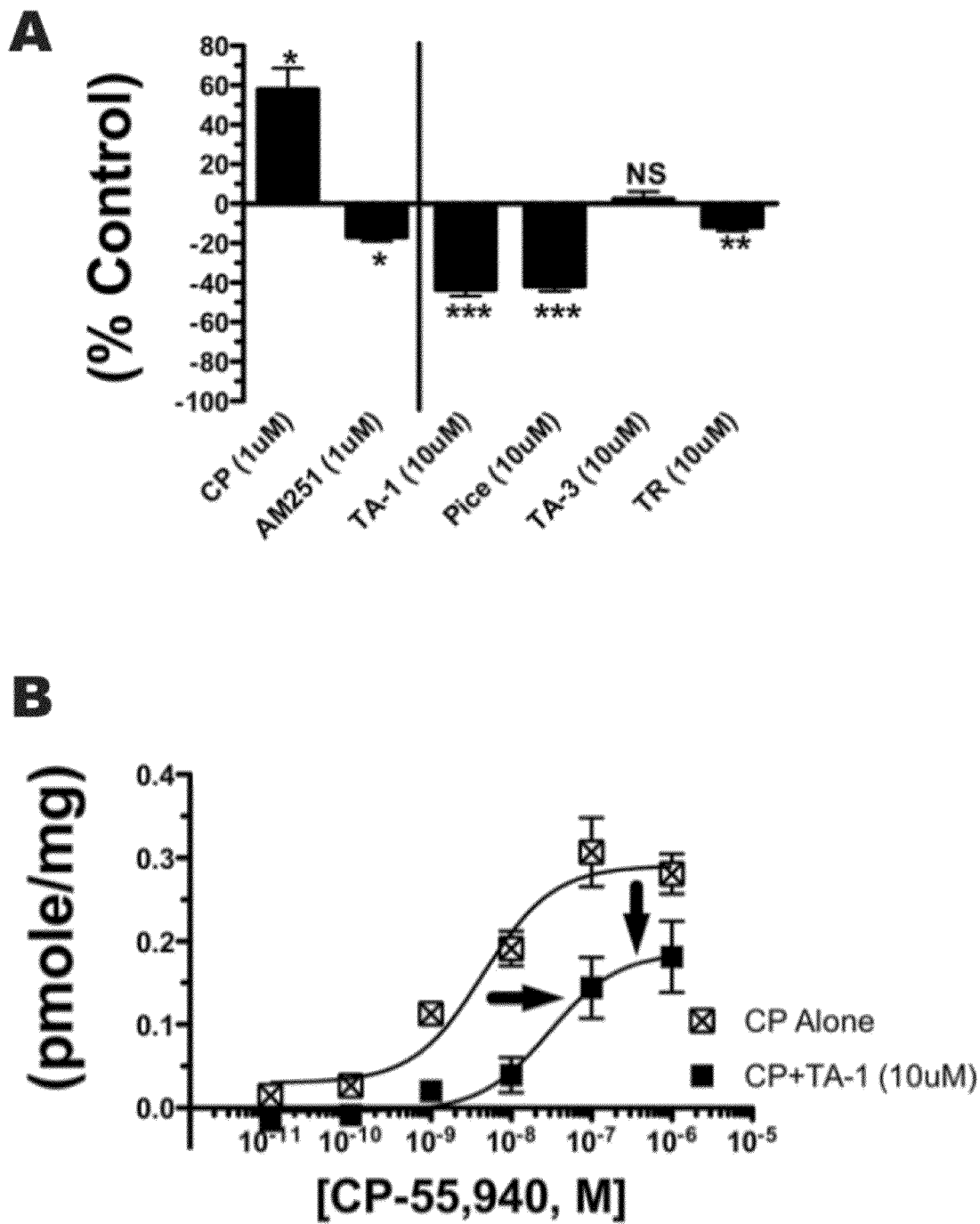
FIG. 7 presents the intrinsic activity of tRes and analogs at CB1 receptors. (A) presents the percent of control G-protein activity in the presence of the indicated compounds. (B) plots $^{35}$S-GTPγS binding in the presence of tA1 and increasing concentration of the CB1 agonist CP-55,940. (C) presents $^{35}$S-GTPγS binding in the presence of tA3 and increasing concentration of CP-55,940. *, **=significantly different ($P<0.05$, $0.01$) from 0%. NS=not significantly different from 0%.

Studies were initiated to determine the intrinsic activity of tRes and its analogs at CB1 receptors by measuring the activity of CB1 receptor-stimulated G-protein activity. For this, mouse brain membranes were incubated with 0.1 nM $^{35}S$-GYPyS and either 1 µM CP-55,940 (CB1 agonist), 1 µM AM251 (CB1 inverse agonist), or 10 µM of tRes (TR), tPice, tA1, or tA3 for 30 min at 30° C., and then filtered As expected CP-55,940 stimulated and AM251 inhibited G-protein activity in mouse brains expressing CB1 receptors (FIG. 7A). Both stimulation and inhibition were blocked by co-incubation with the selective CB1 neutral antagonist 0-2050 (data not shown). It was found; however, that 10 µM of tA-1 and Pice markedly reduced basal G-protein activity, while 10 µM of tA-3 and tRes had little effect on basal G-protein activity. Although it has not been determined whether the potential inverse activity produced by tA-1 and Pice could be mediated by CB1 receptors, clearly none of the tested analogs acted as agonists at CB1 receptors to stimulate G-proteins.

Figure 7C:
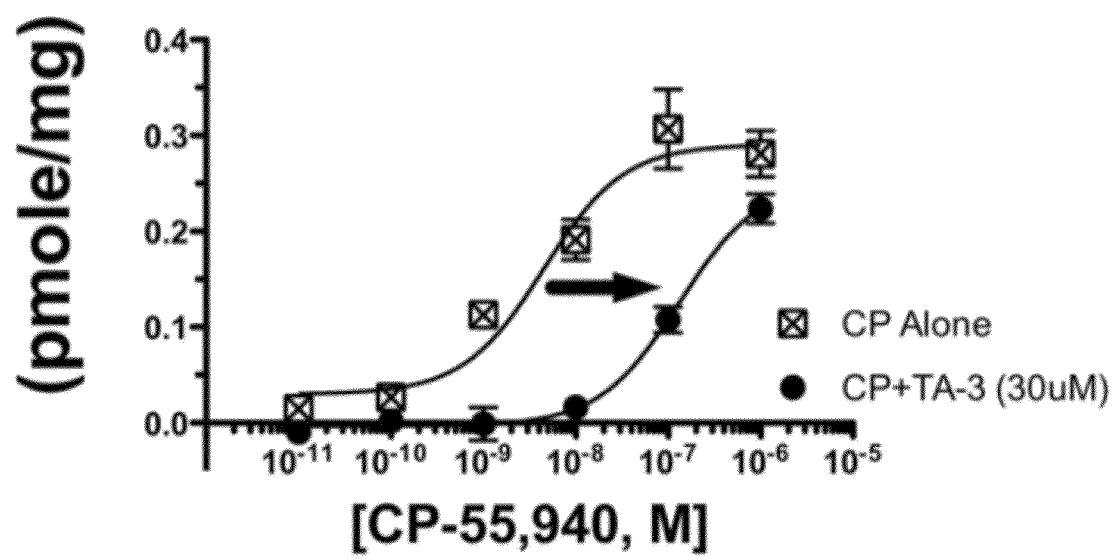

To examine the possible antagonist activity of these compounds, G-protein activity was measured in the presence of tA1 or tA3 and increasing concentrations of the CB1R agonist CP-55,940. It was found that incubation with 10 µM tA-1 or 30 µM of tA-3 appeared to result in CB1R antagonism, producing a 7-fold (4.3 vs 28 nM) or 30-fold (4.3 vs 127 nM) increase (shift-to-the-right) in the $ED_{50}$ required to activate G-proteins by CP-55,940, respectively (FIGS. 7B and 7C). Moreover, in addition to increasing the $ED_{50}$, tA-1 but not tA-3 also significantly reduced the maximal response produced by CP-55,940 from 0.34±0.03 to 0.22±0.04 pmole/mg protein. This indicates that tA-1 may produce CB1 receptor antagonism by both competitive and non-competitive mechanisms.

Example 7

Assessment of Renal Microcirculation after CLP and Administration of tRes

An established murine cecal ligation and puncture model (CLP) of sepsis-induced renal injury was used to assess potency and efficacy of tRes. Control (sham) mice underwent surgery but not CLP. Fresh solutions of tRes were prepared in dimethyl sulfoxide as the vehicle (veh) and diluted in normal saline before use. Dextran and dihydrorhodamine-1,2,3 were administered to the penile vein to visualize the capillary vascular space and detect RNS generation, respectively. The left kidney was exposed by a flank incision and positioned on a glass stage with a fluorescent microscope equipped with an Axiocam HSm camera. Intravital Video Microscopy (IVVM) of 10 s intervals at 200× magnification were acquired from randomly selected, non-overlapping fields of view.

Figure 8:
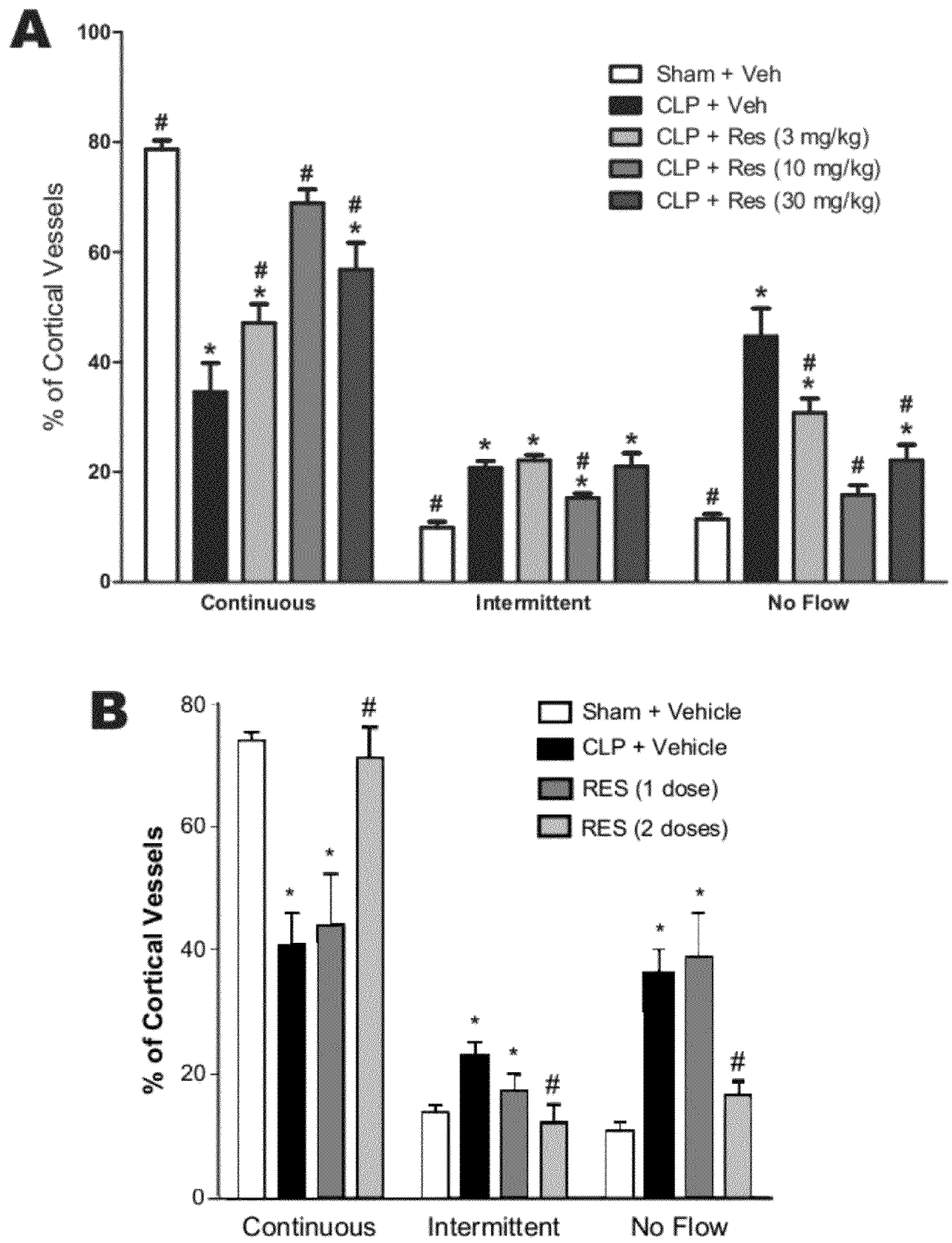
FIG. 8 shows cortical capillary perfusion. (A) shows the effect of tRes (RES) on renal cortical peritubular capillary perfusion at 6 hours. Cecal ligation and puncture (CLP) caused a dramatic reduction in perfusion at 6 hours. tRes administration at 5.5 hours improved categorical perfusion in a bell-shaped, dose-dependent manner with 10 mg/kg being the most efficacious dose. (B) shows the effect of delayed tRes administration on renal capillary categorical perfusion. A single dose of tRes 10 mg/kg at 6 hours was unable to improve capillary perfusion; however, administration of an additional dose resulted in a complete restoration of capillary perfusion. *=significantly different ($P<0.05$) from sham. #=significantly different ($P<0.05$) from CLP.
Figure 9:
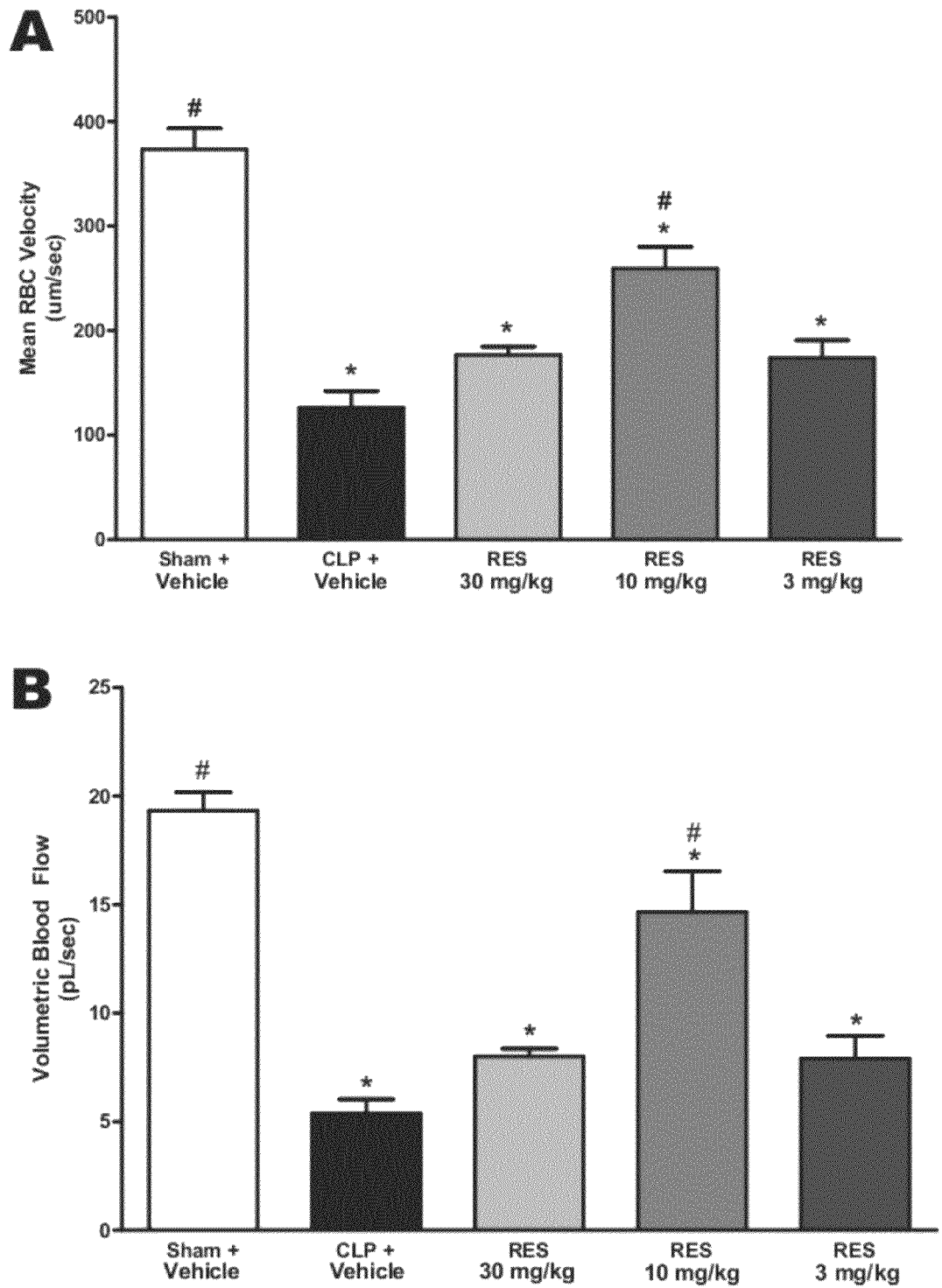
FIG. 9 shows mean red blood cell velocity and renal capillary volumetric blood flow. (A) shows the effect of tRes (RES) on mean red blood cell (RBC) velocity. (B) shows the effect of tRES on renal capillary volumetric blood flow. CLP caused a significant reduction in mean RBC velocity and volumetric blood flow at 6 h. tRes at 6 hours improved both indices in a bell-shaped, dose-dependent manner with 10 mg/kg being the most efficacious dose. (C) and (D) show effects of delayed administration on RBC velocity and volumetric blood flow, respectively. A single dose of tRes post-CLP did not improve either index at 18 hours, however, administration of an additional dose of tRes at 12 hours resulted in a complete restoration of RBC velocity (C) and volumetric blood flow (D). *=significantly different ($P<0.05$) from sham. #=significantly different ($P<0.05$) from CLP.
Figure 9:
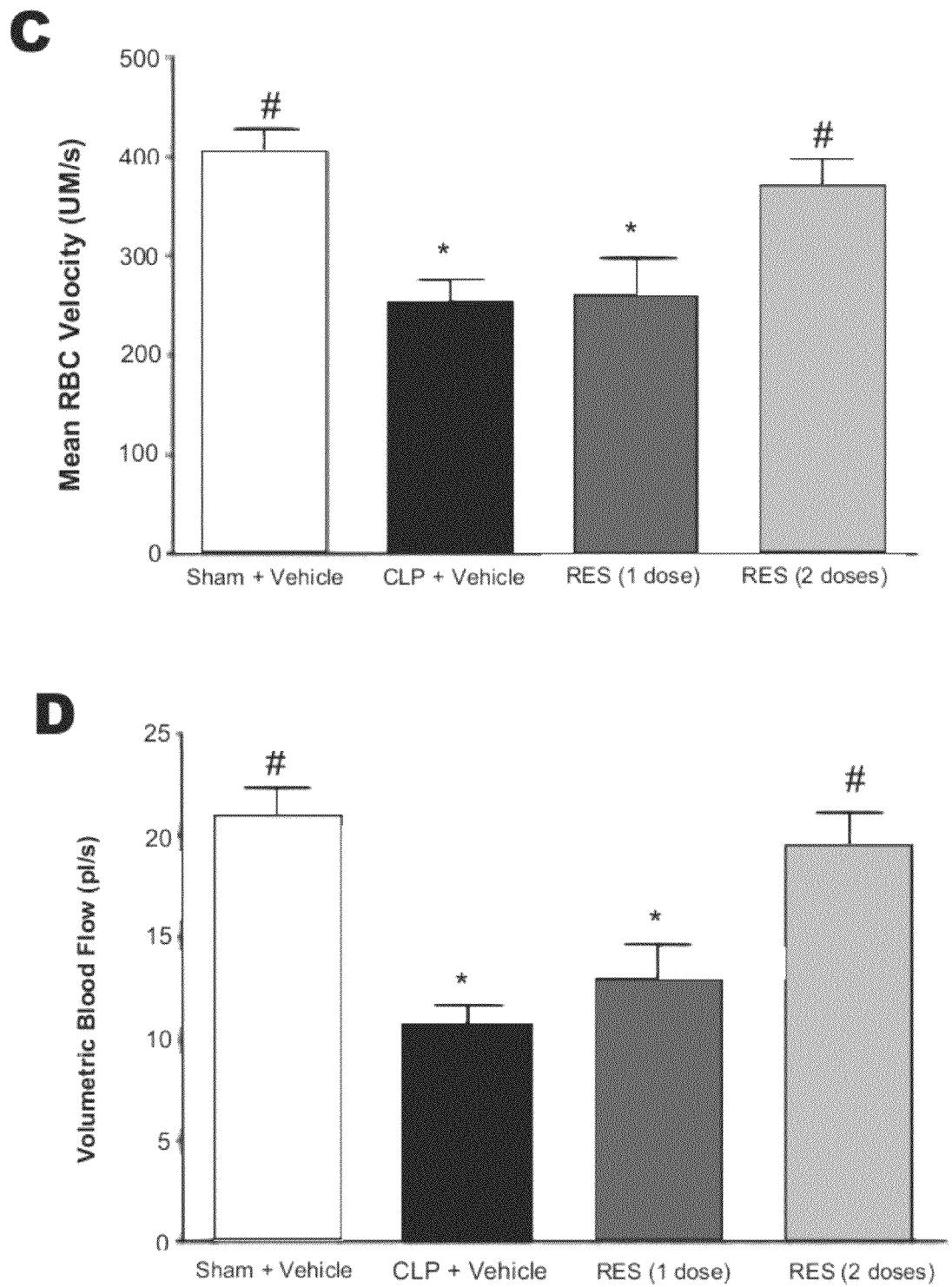

Capillaries were randomly selected for the 10 sec videos and categorized as "continuous flow" where red blood cell (RBC) movement was continuous; "intermittent flow" where RBC movement stopped or reversed; or "no flow" where no RBC movement was detected as shown in FIG. 8. RBC velocity was calculated in continuously flowing capillaries by measuring the distance traveled by a single RBC over time, expressed in µm/s. CLP caused a dramatic reduction in perfusion at 6 hours, tRes administration at 5.5 hours improved perfusion in a dose dependent manner with 10 mg/kg being the most efficacious dose as shown in FIG. 8. CLP caused a significant reduction in mean RBC velocity and renal capacity. tRes improved both indices of RBC velocity and volumetric blood flow as shown in FIGS. 9A and 9B, respectively.

At 18 hours following CLP, capillary perfusion was still depressed relative to Sham. A single dose of tRes (10 mg/kg) administered at 6 hours was unable to maintain perfusion through 18 hours. However, a second dose administered at 12 hours prevented the change. See FIGS. 9(C)-9(D).

Example 8

Detection of RNS Generation Using IVVM and Anti-Nitrotyrosine Staining

Figure 10:
FIG. 10 shows the effect of tRes (RES) administration on reactive nitrogen species (RNS) generation in the renal tubules at 18 hours. Representative images of rhodamine fluorescence are shown in (A)-(C) at 200× magnification. Quantification of rhodamine fluorescence is shown in (D). CLP increased the generation of RNS in the renal tubules compared to Control (Sham). A single dose of tRes at 6 hours partially blocked rhodamine fluorescence, whereas, a second dose at 12 hours completely blocked rhodamine fluorescence (D) shows the quantification of fluorescence. (E)-(F) show the cumulative generation over 18 hours of nitrotyrosine-protein adducts as shown by immunoreactive anti-nitrotyrosine staining. Tissue from Control (sham) mice (E) showed faint and specific staining. Tissue from CLP mice show strong specific staining localized to the tubules (F). Tissue from mice with CLP treated with two doses of tRes showed little specific staining (G).
Figure 10:
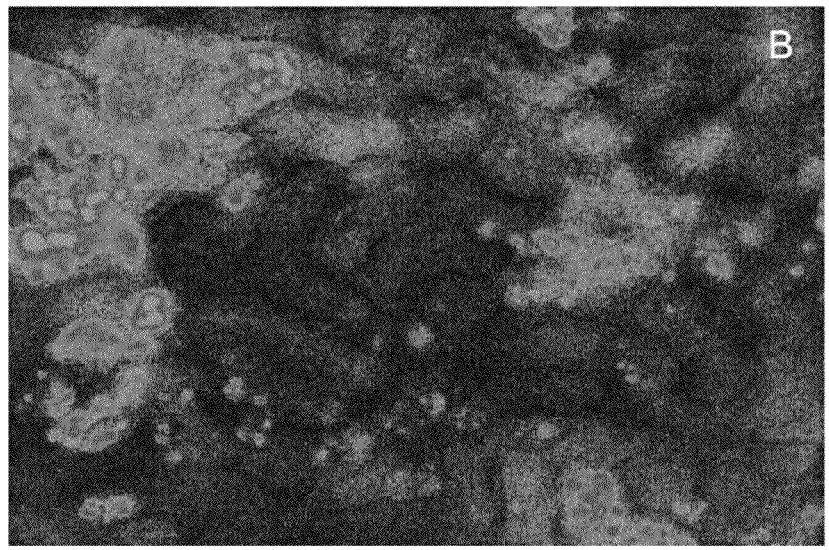
Figure 10:
Figure 10:
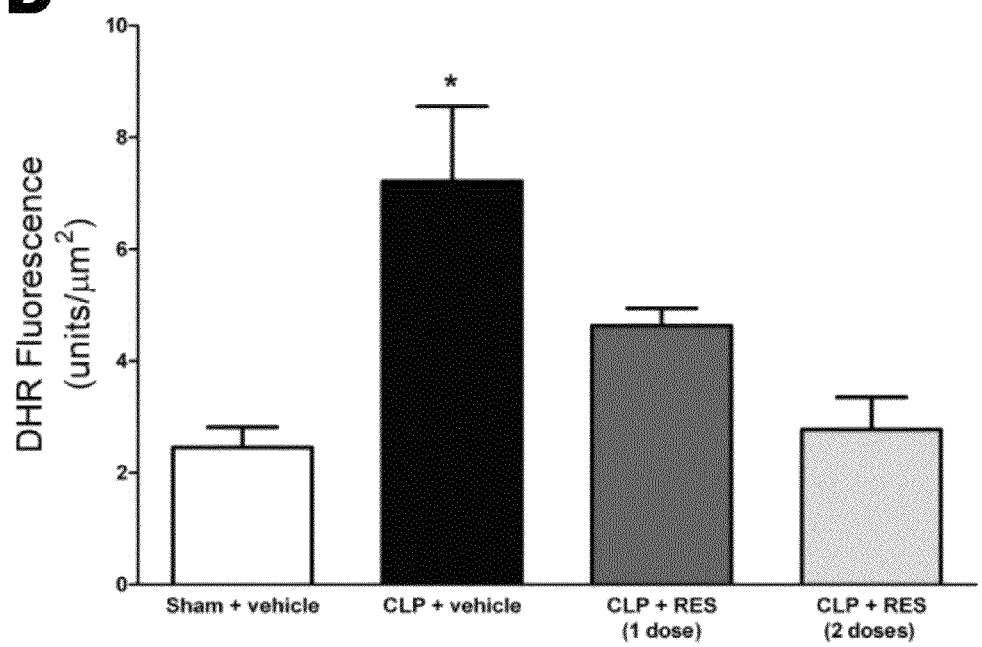
Figure 10:
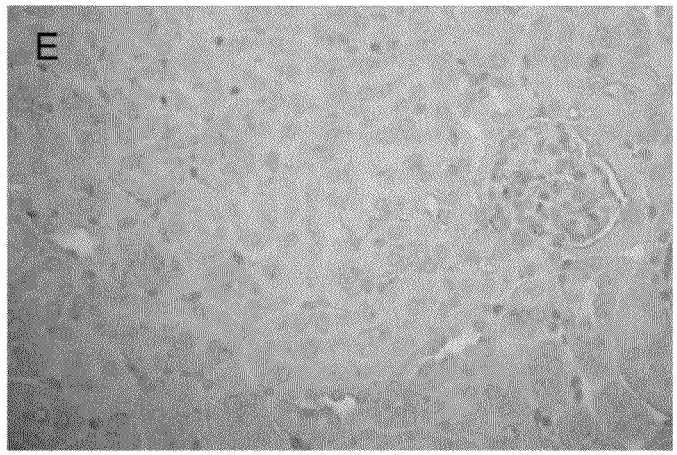
Figure 10:
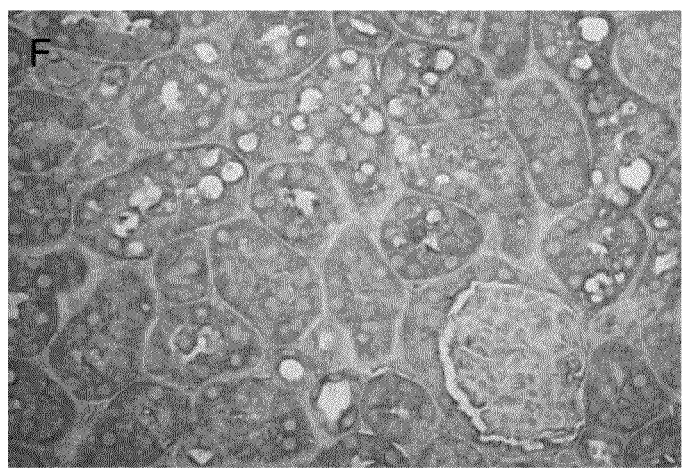
Figure 10:
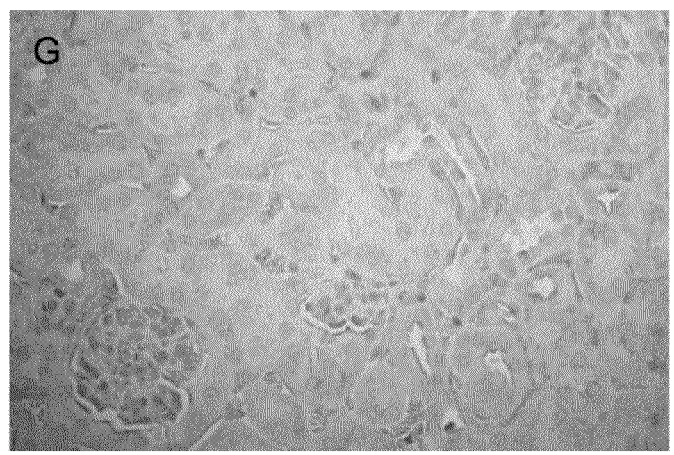

The reactive nitrogen species peroxynitrite preferentially oxidizes DHR to fluorescent rhodamine that is visualized at 535 nm excitation and 590 nm emission. Still images exposed for 500 ms were captured from fields of view used to determine capillary perfusion. Fluorescence intensity was measured by ImageJ (National Institutes of Health, Bethesda, Md.) after first subtracting background fluorescence intensity. Representative images of fluorescence are shown in FIG. 10, panels (A)-(C), and the quantification of fluorescence is shown in FIG. 10 panel D. Data are expressed as arbitrary units/μg. CLP increased the generation of RNS in the renal tubules compared to Control (Sham). A single dose of tRes at 6 hours partially, but significantly reduced rhodamine fluorescence, whereas, a second dose at 12 hours completely blocked rhodamine fluorescence.

Figure 12:
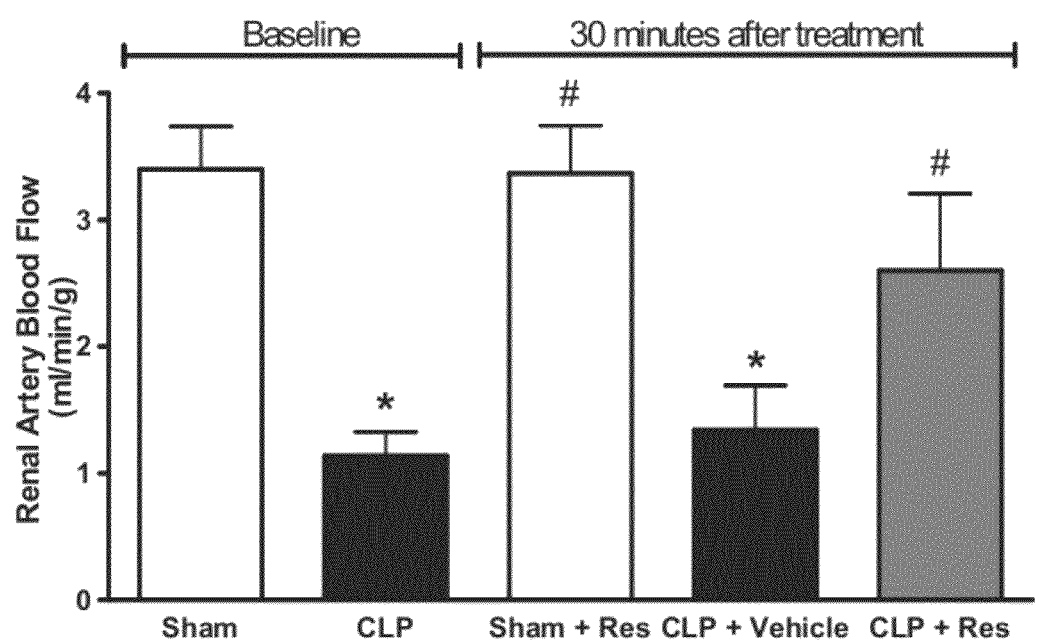
FIG. 12 shows baseline and treatment with tRES on renal arterial blood flow. CLP caused a significant reduction in renal arterial blood flow at 6 hours. tRes administration at 5.5 hours improved blood flow in CLP mice but was without effect in Control (Sham) mice. *=significantly different (P<0.05) from sham. #=significantly different (P<0.05) from CLP.

Nitrotyrosine-protein adducts were detected using a polyclonal anti-nitrotyrosine antibody (Millipore, Billerica, Mass.) diluted 1:1, 200 in 1% BSA, 0.5% milk in 1× Tris-buffered saline, pH 7.6. Antigens were unmasked using 10 mM citrate (pH 6.0) and 95° C. for 30 min. Gill's hematoxylin II was used as a counterstain. Pre-incubation of the anti-nitrotyrosine antibody with 10 mM nitrotyrosine was used as the nonspecific binding control. FIG. 12 (E)-(G) show nitrotyrosine staining. After CLP, nitrotyrosine was intense in renal tubules but not in glomeruli. Two doses of tRes blocked formation of nitrotyrosine adducts.

Example 9

Measurement of Mean Arterial Pressure and Heart Rate

Figure 11:
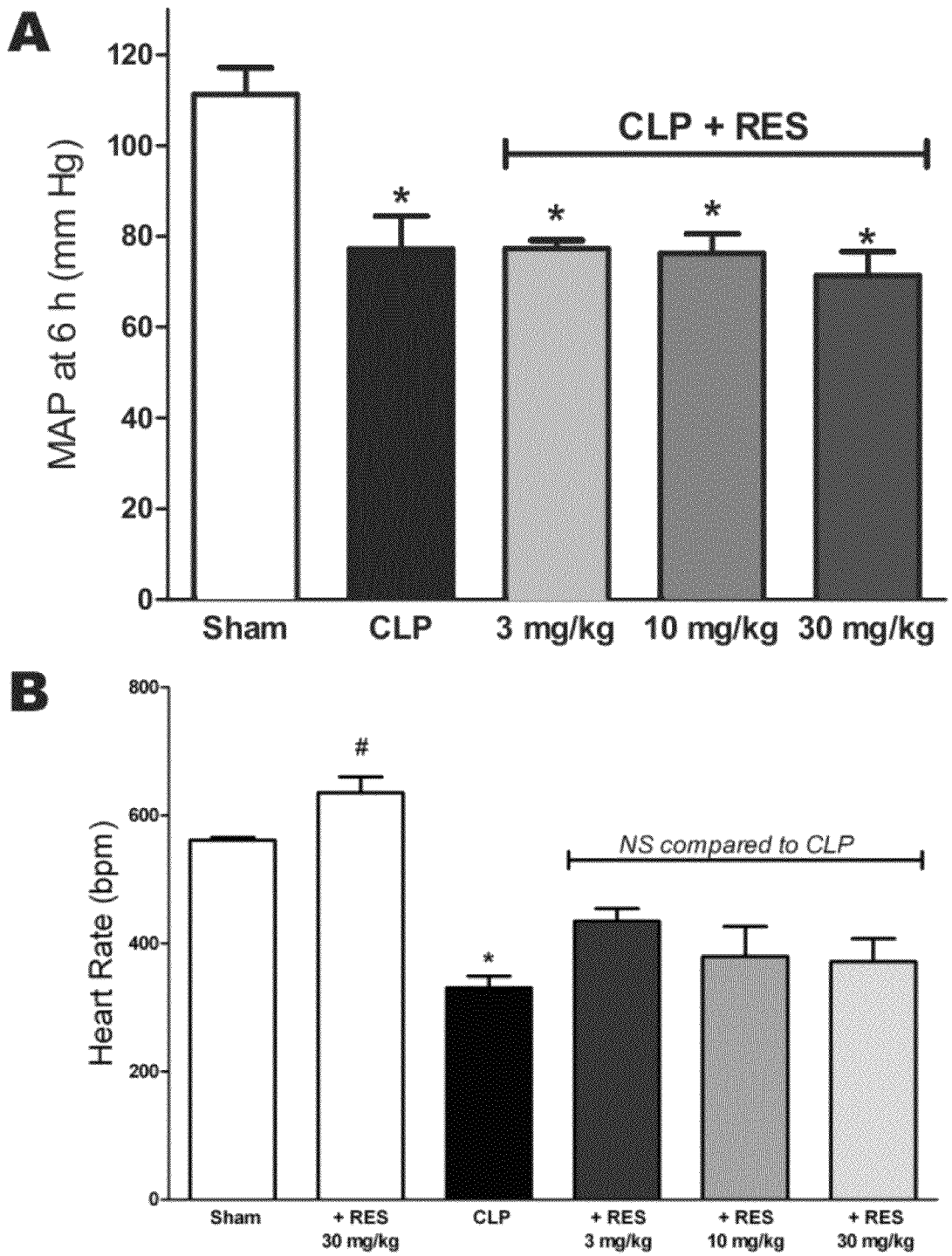
FIG. 11 shows that CLP caused a dramatic fall in mean arterial pressure (MAP) (A) and heart rate (HR) (B) at 6 hours. tRes had no effect of MAP or HR in CLP mice. However, RES did slightly increase HR in Control (Sham). *=significantly different ($P<0.05$) from sham by ANOVA. #=significantly different ($P<0.05$) from CLP.

Mean arterial pressure (MAP) and heart rate (HR) were monitored continuously in conscious mice using biotelemetry. Transmitters (Data Sciences International, Minneapolis Minn.) were implanted into the carotid artery under isoflurane anesthesia and the animals were allowed to recover for 48 h. Mice were re-anesthetized with isoflurane and received CLP or Control (Sham) surgery. Cardiovascular parameters were recorded for 10 s every 5 min. At 5.5 hours following surgery, mice were administered tRes (3, 10, or 30 mg/kg i.p.) or vehicle. Results are shown in FIG. 11 (A)-(B). CLP caused a dramatic fall in MAP from 111±7 mmHg to 77±7 mmHg, see FIG. 11A, and heart rate, see FIG. 11B, at 6 hours. tRes had no effect of MAP or HR in CLP mice however, RES did slightly increase HR in Control (Sham).

Example 10

Measurement of Renal Arterial Blood Flow

Under isoflurane anesthesia, the right kidney was exposed by flank incision and the renal artery and vein were carefully dissected from surrounding tissue with Dumont-5 forceps. The renal artery was isolated from the vein and a Transonic Systems (Ithaca, N.Y.) 0.5 PSL renal artery Doppler flow probe was positioned around the renal artery. The probe was calibrated in water using the zero and scale settings on the TS420 flowmeter (Transonic Systems). Renal Arterial Blood Flow (RBF) was recorded after the flow stabilized (approximately 10 min after placement of the probe) using PowerLab and LabChart software (AD Instruments, New Zealand). tRes (RES) (10 mg/kg) or vehicle was administered via the penile vein. Body temperature was maintained at 36 to 37° C. with a heating lamp. Data were expressed in ml/min/g kidney weight. FIG. 12 shows the results. CLP caused a significant reduction in RBF at 6 hours. tRes administration at 5.5 hours improved RBF in CLP mice from 1.1±0.2 ml/min/g to 2.6±0.6 ml/min/g but was without effect in Control (Sham) mice. The increase in RBF was likely due to decrease in renal vascular resistance because tRes did not raise MAP or HR.

Example 11

Measurement of Systemic Serum Nitric Oxide Levels

Serum nitrate and nitrate levels were determined using the Total Nitric Oxide Assay Kit (Assay Designs, Ann Arbor, Mich.) as directed by the manufacturer. Data were expressed as serum nitrate+nitrate concentration in μm. At 18 hours, levels in CLP mice were significantly higher than in Control (sham), 166±16 μM and 60±6 μM, respectively. Two doses of tRES did not affect serum nitrate+nitrate concentration.

Example 12

Measurement of Serum Creatinine and Blood Urea Nitrogen Levels

Figure 13:
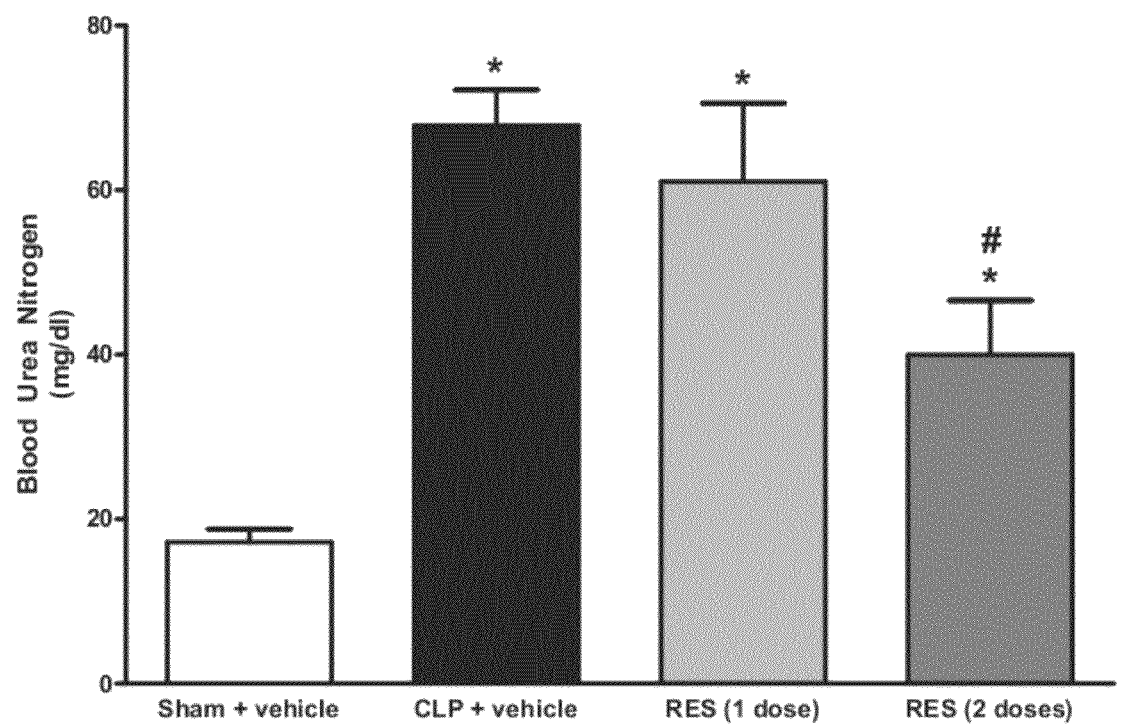
FIG. 13 shows the effect of tRes (RES) on morphology and serum levels of blood urea nitrogen (BUN) at 18 hours. At 18 hours post-CLP, BUN levels were significantly increased. A single dosage of tRes reduced BUN levels, but a second dose at 12 hours significantly reduced BUN levels. *=significantly different (P<0.05) from sham. #=significantly different (P<0.05) from CLP.
Figure 14:
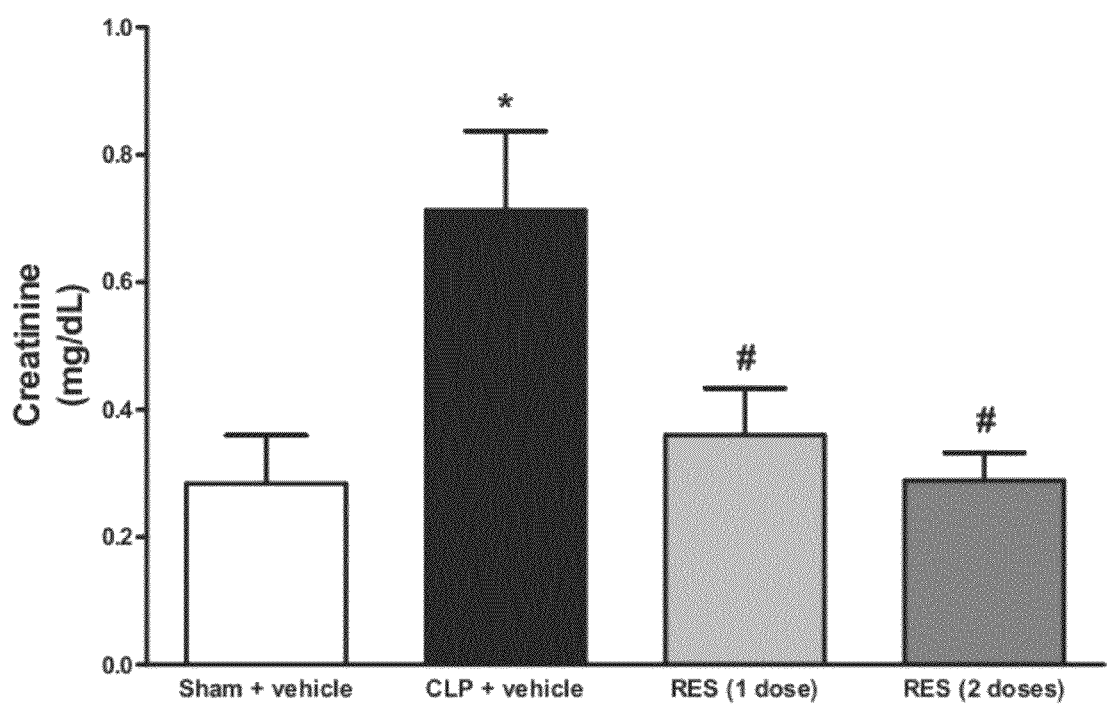
FIG. 14 shows the effect of tRes (RES) on morphology and serum levels of creatinine at 18 hours. At 18 hours post-CLP, creatinine levels were significantly increased. A single dosage of tRes was effective at reducing creatinine levels, while a second dose at 12 hours did not further reduced creatinine levels. *=significantly different (P<0.05) from sham. #=significantly different (P<0.05) from CLP.

Acute Kidney Injury (AKI) is accompanied by elevated blood urea nitrogen levels, elevated creatinine levels, and low blood pressure. Serum creatinine and blood urea nitrogen (BUN) were measured using the QuantiChrom® Creatinine Assay kit and Urea Assay Kit (BioAssay Systems, Hayward Calif.). RES (10 mg/kg) administered 6 hours after CLP surgery significantly reduced serum creatinine levels, but not BUN levels. However, when an additional dose of tRes was given at 12 h there was significant reduction in both BUN and serum creatinine levels as shown in FIG. 13 and FIG. 14, respectively.

Example 13

Histology of Renal Tissue

Figure 15:
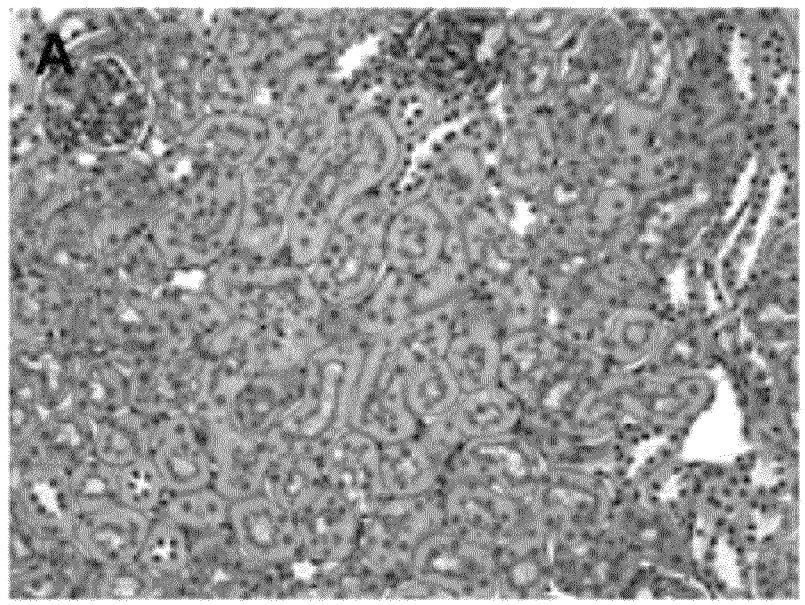
FIG. 15 shows representative PAS-stained sections in (A)-(C), tissue injury scores are shown in (D). CLP caused mild morphological changes characterized by loss of brush border, cast formation, vacuolization, and tube dilation. These changes were prevented by the two-dose regimen of tRes. *=significantly different (P<0.05) from sham.
Figure 15:
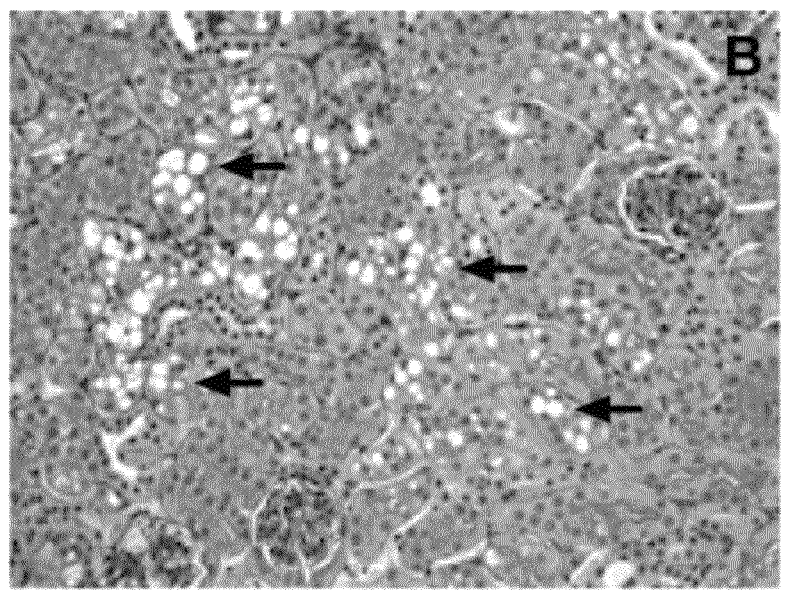
Figure 15:
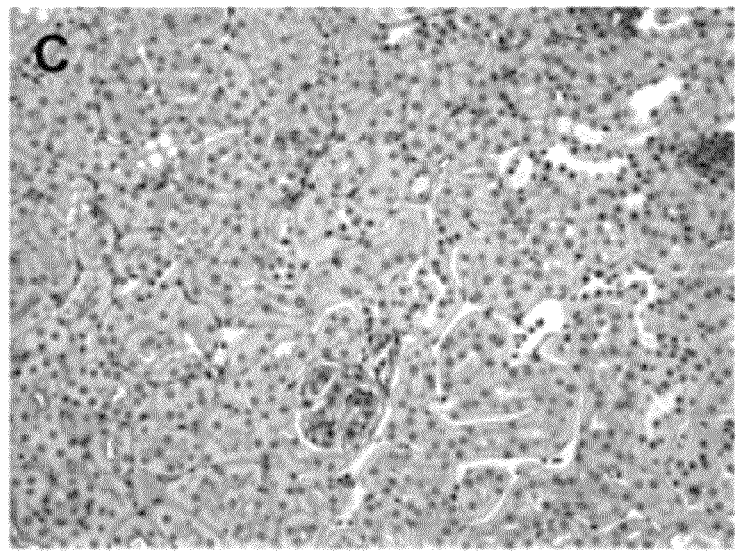
Figure 15:
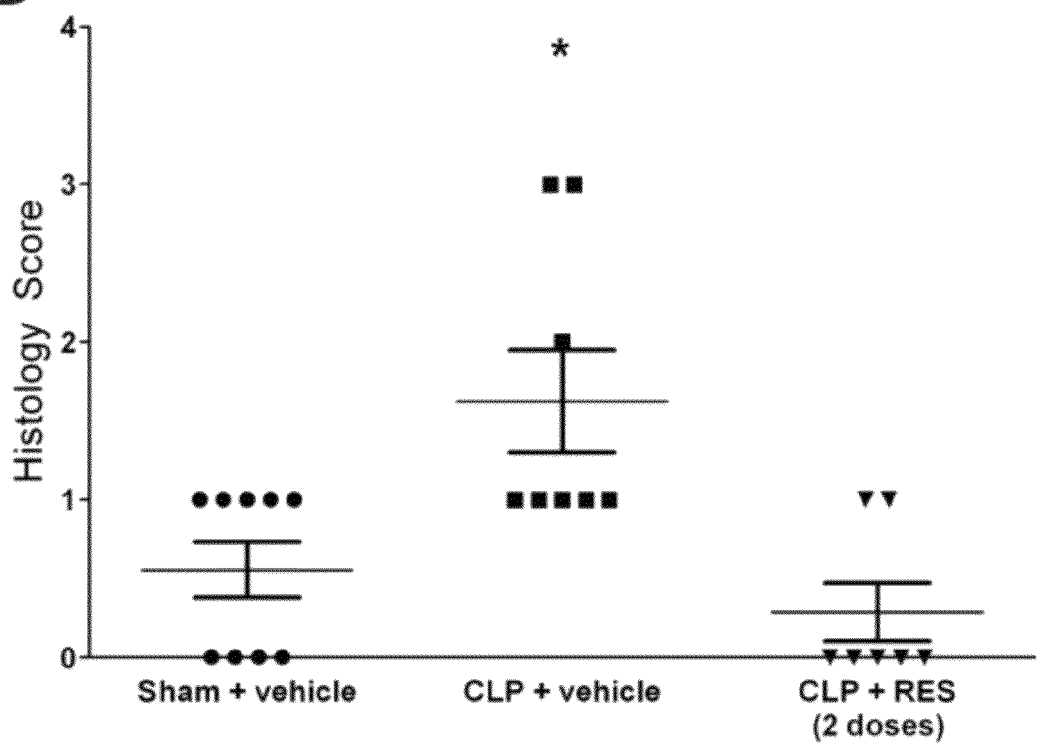

Renal tissue was also stained with periodic acid-Schiff staining to show the amount of injury to the tissue. The periodic acid-Schiff (PAS) stained sections were scored in a blinded, semi-quantitative manner. For each animal, at least 10 high power (400×) fields were examined. The percentage of tubules that displayed cellular necrosis, loss of brush border, cast formation, vacuolization, and tubule dilation were scored as follows: 0=none, 1=<10%, 2=11-25%, 3=26-45%, 4=46-75%, and 5=>76%. Representative PAS-stained sections are shown in FIG. 15, panels (A)-(C) 200× magnification and the tissue scores are shown in (D). CLP caused mild morphological changes characterized by brush border, cast formation, vacuolization, and tubule dilation. These changes were prevented by the two-dose regimen of tRes.

Example 14

Survival Study After CLP

Figure 16:
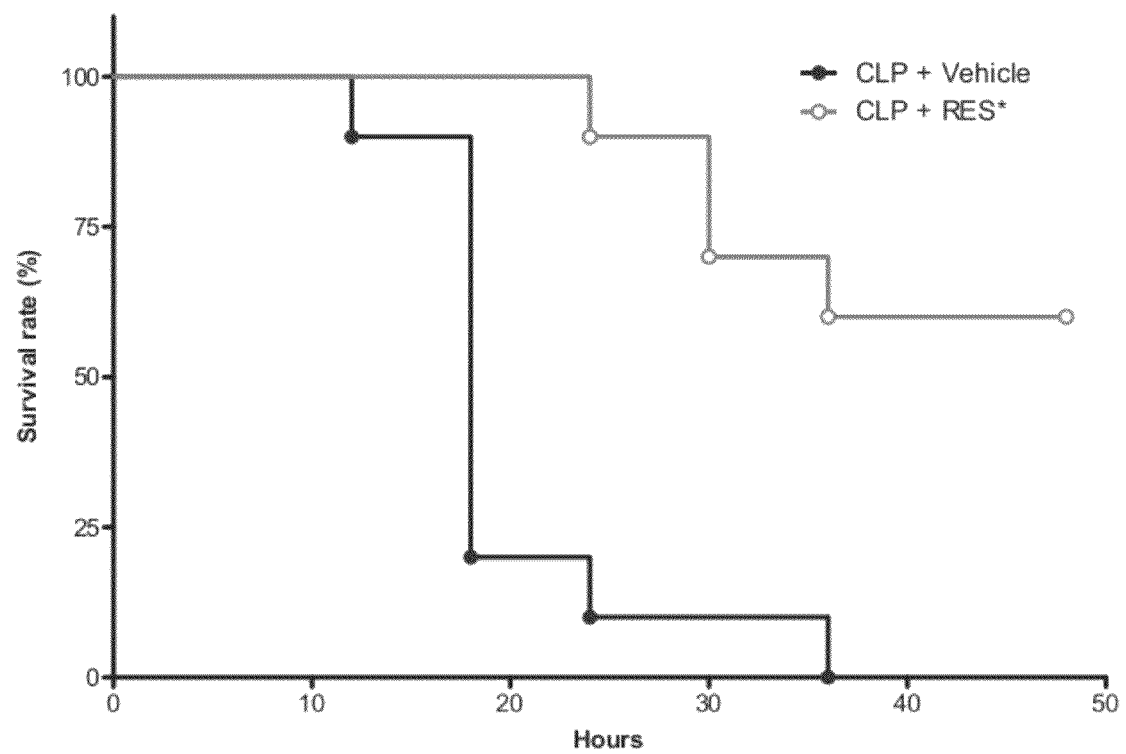
FIG. 16 shows the effects of tRes (RES) on survival after CLP. Administration of tRes at 6, 12, and 18 hours resulted in a significant increased survival compared to the Control (CLP+Vehicle).

Mice subjected to CLP surgery were administered either tRes (10 mg/kg) or vehicle at 6, 12, and 18 hours following CLP and monitored for 48 h. Core body temperature was used as an indicator of pending mortality (Warn, Pa., Brampton MW, Sharp A, et al. Infrared body temperature measurement of mice as an early predictor of death in experimental fungal infections. *Lab. Anim.* 2003, 37: 126-131) and was measured every 6 hours using a rectal probe. As shown in FIG. 16, treatment at 6, 12, and 18 h significantly improve survival in CLP mice.

Example 15

Reversal of Reduced Renal Blood Flow after CLP

Figure 17:
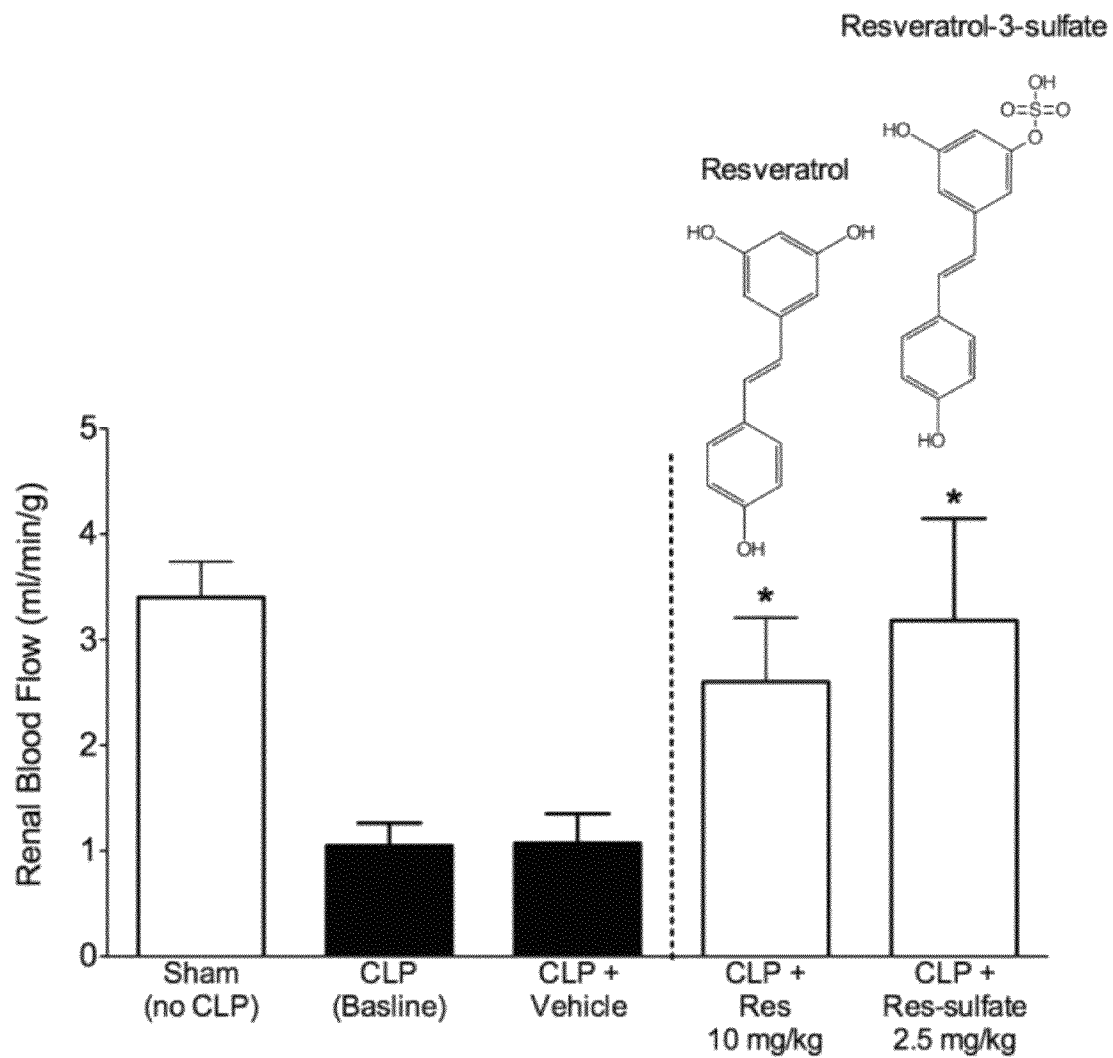
FIG. 17 illustrates that tRes and tRes-3-sulfate increased renal blood flow after CLP. Shown is renal blood flow (ml/min/g) in sham treated mice, CLP-treated mice, CLP plus vehicle, CLP plus Res, and CLP plus Res-sulfate. n=4-7 mice/group. *P<0.05 compared to CLP and CLP plus vehicle.

Renal blood flow was measured essentially as described above in Example 10 following CPL surgery or control treatment (no surgery). CPL-treated mice were administered 10 mg/kg of resveratrol, 2.5 mg/kg of resveratrol-3-sulfate, or vehicle. The results are shown in FIG. 17. Administration of either resveratrol or resveratrol-3-sulfate increased blood flow in the CPL-treated mice. In fact, resveratrol-3-sulfate produced the same degree of reversal at 25% of the dose of resveratrol.

What is claimed is:

1. A method for improving renal blood flow and microcirculation during sepsis, the method comprising administering a monomer or an oligomer of a compound of Formula (I) to a subject experiencing sepsis such that renal blood flow and microcirculation of the subject are improved, the compound of Formula (I):

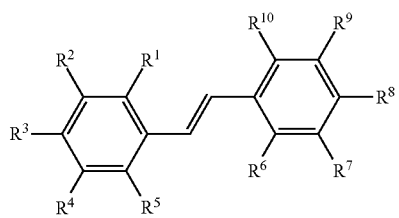

(I)

wherein:
$R^1$, $R^2$, $R^3$, $R^4$, $R^5$, $R^6$, $R^7$, $R^8$, $R^9$, and $R^{10}$ are independently hydrogen, hydroxyl, hydrocarbyl, substituted hydrocarbyl, hydrocarbyloxy, substituted hydrocarbyloxy, or sulfoxy; provided that at least one of the R groups is a hydroxyl or substituted hydroxyl group; and provided that if the compound of Formula (I) is monomeric, then the compound of Formula (I) is other than a compound in which $R^1$, $R^3$, $R^5$, $R^6$, $R^7$, and $R^{10}$ are hydrogen, $R^2$, $R^4$, and $R^8$ are independently hydroxyl, alkoxy, or glucosyloxy, and $R^9$ is hydrogen or hydroxyl.

2. The method of claim 1, wherein $R^1$, $R^2$, $R^3$, $R^4$, $R^5$, $R^6$, $R^7$, $R^8$, $R^9$, and $R^{10}$ are independently hydrogen, hydroxyl, alkyl, alkenyl, alkyoxy, alkenyloxy, aryloxy, glucuronidyloxy, glucosyloxy, or sulfoxy.

3. The method of claim 1, wherein $R^1$, $R^5$, $R^6$, $R^7$, $R^9$, and $R^{10}$ are hydrogen; $R^3$ is alkenyl; and $R^2$, $R^4$, and $R^8$ are independently hydroxyl, alkoxy, glucuronidyloxy, or sulfoxy.

4. The method of claim 1, wherein $R^1$, $R^5$, $R^6$, $R^9$, and $R^{10}$ are hydrogen; $R^3$ is hydroxyl or alkenyl; and $R^2$, $R^4$, $R^7$, and $R^8$ are independently hydroxyl, alkoxy, glucuronidyloxy, or sulfoxy.

5. The method of claim 1, wherein the compound of Formula (I) is a cis isomer or a trans isomer.

6. The method of claim 1, wherein the oligomer of the compound of Formula (I) comprises cis isomers, trans isomers, or a combination of cis and trans isomers.

7. The method of claim 1, wherein the subject is a rodent, a research animal, a companion animal, an agricultural animal, or a human.

8. The method of claim 1, wherein the half life of the compound of Formula (I) is greater than about 30 minutes.

9. The method of claim 1, wherein the compound is administered to the subject in an amount ranging from about 10 mg to about 30 mg per kilogram of the subject, and the compound is administered to the subject once every 4 to 6 hours for about 24 hours.

10. The method of claim 1, wherein the compound is administered to the subject in an amount of about 10 mg per kilogram of the subject, and the compound is administered to the subject once every six hours for about 18 hours.

11. A method for treating acute kidney injury during sepsis, the method comprising administering a monomer or an oligomer of a compound of Formula (I) to a subject experiencing sepsis, such that acute kidney injury in the subject is treated, the compound of Formula (I):

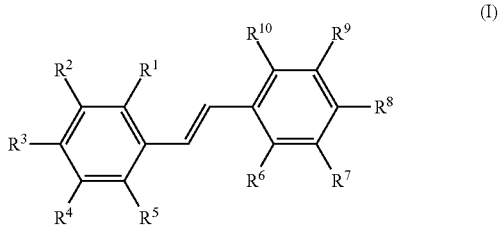

(I)

wherein:
$R^1$, $R^2$, $R^3$, $R^4$, $R^5$, $R^6$, $R^7$, $R^8$, $R^9$, and $R^{10}$ are independently hydrogen, hydroxyl, hydrocarbyl, substituted hydrocarbyl, hydrocarbyloxy, substituted hydrocarbyloxy, or sulfoxy; provided that at least one of the R groups is a hydroxyl or substituted hydroxyl group; and provided that if the compound of Formula (I) is monomeric, then the compound of Formula (I) is other than a compound in which $R^1$, $R^3$, $R^5$, $R^6$, $R^7$, and $R^{10}$ are hydrogen, $R^2$, $R^4$, and $R^8$ are independently hydroxyl, alkoxy, or glucosyloxy, and $R^9$ is hydrogen or hydroxyl.

12. The method of claim 11, wherein $R^1$, $R^2$, $R^3$, $R^4$, $R^5$, $R^6$, $R^7$, $R^8$, $R^9$, and $R^{10}$ are independently hydrogen, hydroxyl, alkyl, alkenyl, alkyoxy, alkenyloxy, aryloxy, glucuronidyloxy, glucosyloxy, or sulfoxy.

13. The method of claim 11, wherein $R^1$, $R^5$, $R^6$, $R^7$, $R^9$, and $R^{10}$ are hydrogen; $R^3$ is alkenyl; and $R^2$, $R^4$, and $R^8$ are independently hydroxyl, alkoxy, glucuronidyloxy, or sulfoxy.

14. The method of claim 11, wherein $R^1$, $R^5$, $R^6$, $R^9$, and $R^{10}$ are hydrogen; $R^3$ is hydroxyl or alkenyl; and $R^2$, $R^4$, $R^7$, and $R^8$ are independently hydroxyl, alkoxy, glucuronidyloxy, or sulfoxy.

15. The method of claim 11, wherein the compound of Formula (I) is a cis isomer or a trans isomer.

16. The method of claim 11, wherein the oligomer of the compound of Formula (I) comprises cis isomers, trans isomers, or a combination of cis and trans isomers.

17. The method of claim 11, wherein the subject is a rodent, a research animal, a companion animal, an agricultural animal, or a human.

18. The method of claim 11, wherein the half life of the compound of Formula (I) is greater than about 30 minutes.

19. The method of claim 11, wherein the compound is administered to the subject in an amount ranging from about 10 mg to about 30 mg per kilogram of the subject, and the compound is administered to the subject once every 4 to 6 hours for about 24 hours.

20. The method of claim 11, wherein the compound is administered to the subject in an amount of about 10 mg per kilogram of the subject, and the compound is administered to the subject once every six hours for about 18 hours.

* * * * *